US005850016A

United States Patent [19]
Jung et al.

[11] Patent Number: 5,850,016
[45] Date of Patent: Dec. 15, 1998

[54] ALTERATION OF AMINO ACID COMPOSITIONS IN SEEDS

[75] Inventors: Rudolf Jung, Des Moines; Craig Hastings, Perry; Sean Coughlan, Des Moines; David Hu, Johnston, all of Iowa

[73] Assignee: Pioneer Hi-Bred International, Inc., Des Moines, Iowa

[21] Appl. No.: 618,911

[22] Filed: Mar. 20, 1996

[51] Int. Cl.⁶ ............................ C12N 5/04; C12N 15/29; C12P 21/00; C12Q 1/68

[52] U.S. Cl. ............................ 800/205; 435/6; 435/69.1; 435/172.1; 435/320.1; 435/410; 435/415; 536/23.1; 536/23.4; 536/23.6; 800/250

[58] Field of Search .......................... 435/6, 69.1, 172.1, 435/320.1, 410, 415; 536/23.1, 23.4, 23.6; 800/205, 250

[56] References Cited

U.S. PATENT DOCUMENTS

5,003,045   3/1991   Hoffman .............................. 530/378

FOREIGN PATENT DOCUMENTS

0 318 341     5/1989   European Pat. Off. .
WO 94/10315   5/1994   WIPO .
WO 95/27068  10/1995   WIPO .

OTHER PUBLICATIONS

Stitt et al "Regulation of Metabolism in Transgenic Plants" An. Rev. Plant Physiol. Plant Mol. Biol. vol. 46:341–368, 1995.

Karchi, et al.; "Seed–Specific Expression of a Bacterial Desensitized Aspartate Kinase Increases the Production of Seed Threonine and Methionine in Transgenic Tobacco" *The Plant Journal*; vol. 3 (5); pp. 721–727; (1993).

Shewry, et al.; "Seed Storage Proteins: Structures and Biosynthesis" *The Plant Cell*; vol. 7; pp. 945–956; (1995).

George, et al.; "A Novel Methionine–Rich Protein in Soybean Seed: Identification Amino Acid Composition, and N–Terminal Sequence" *J. Agric. Food Chem.*; vol. 39; pp. 224–227; (1991).

Coulter, et al.; "Characterization of a Small Sulphur–Rich Storage Albumin in Seeds of Alfalfa (Medicago sativa L.)" *J. Exp. Bot.*; vol. 41 (233); pp. 1541–1547; (1990).

Mak, et al.; "The Amino Acid Sequence of Wheat β–Purothionin" *Can. J. Biochem.*; vol. 22 (10); PP. 835–842; (1976).

Pedersen, et al.; "Sequence Analysis and Characterization of a Maize Gene Encoding a High–Sulfur Zein Protein of $M_r$ 15,000" *J. Biol. Chem.*; vol. 261 (14); pp. 6279–6284; (1986).

Kirihara, et al.; "Isolation and Sequence of a Gene Encoding a Methionine–Rich 10–KDa Zein Protein from Maize" *Gene*; vol. 71; pp. 359–370; (1988).

Masumura, et al.; "cDNA Cloning of an mRNA Encoding a Sulfur–Rich 10 kDa Prolamin Polypeptide in Rice Seeds" *Plant Mol. Biol.*; vol. 12; pp. 123–130; (1989).

Thompson, et al.; "Structural Elements Regulating Zein Gene Expression" *BioEssays;* vol. 10 (4); pp. 108–113; (1989).

Phillips, et al.; "Induction and Development of Somatic Embryos from Cell Suspension Cultures of Soybean" *Plant Cell Tissue Organ Culture;* vol. 1; pp. 123–129; (1981).

Paterson, et al.; "Regeneration of *Helianthus Annuus* Inbred Plants from Callus" *Plant Sci.;* vol. 42; pp. 125–132; (1985).

Wright, et al.; "Regeneration of Soybean (Glycine max L. Merr.) from Cultured Primary Leaf Tissue" *Plant Cell Reports;* vol. 6, pp. 83–89; (1987).

Barwale, et al.; "Plant Regeneration from Callus Cultures of Several Soybean Genotypes via Embryogenesis and Organogenesis" *Planta;* vol. 167; pp. 473–481; (1986).

Schagger, et al.; "Tricine–Sodium Dodecyl Sulfate–Polyacrylamide Gel Electrophoresis for the Separation of Proteins in the Range from 1 to 100 kDa" *Anal. Biochem.;* vol. 166; pp. 368–379; (1987).

Matsudaira; "Sequence from Picomole Quantities of Proteins Electroblotted onto Polyvinylidene Difluoride Membranes" *J. Biol. Chem.;* vol. 262 (21); pp. 10035–10038; (1987).

Faye, et al.; "Characterization of N–Linked Oligosaccharides by Affinoblotting with Concanavalin A–Peroxidase and Treatment of the Blots with Glycosidases" *Anal. Biochem.;* vol. 149; pp. 218–224; (1985).

Kollipara, et al.; "Characterization of Trypsin and Chymotrypsin Inhibitors in the Wild Perennial Glycine Species" *J. Agri. Food Chem;* vol. 40; pp. 2356–2363 (1992).

de Lumen, et al.; "Identification of Methionine–Containing Proteins and Quantitation of Their Methione Contents" *J. Agric. Food Chem.;* vol. 35; pp. 688–691; (1987).

Kho, et al.; "Identification and Isolation of Methionine–Cysteine Rich Proteins in Soybean Seed" *Plant Food Hum. Nutr.;* vol. 38; pp. 287–296; (1988).

Gayler, et al.; "Biosynthesis, cDNA and Amino Acid Sequences of a Precursor of Conglutin δ, a Sulphur–Rich Protein from Lupinus angustifolius" *Plant Mol. Biol.;* vol. 15; pp. 879–893; (1990).

Shure, et al.; "Molecular Identification and Isolation of the Waxy Locus in Maize" *Cell;* vol. 35; pp. 225–233; (1983).

(List continued on next page.)

*Primary Examiner*—John LeGuyader
*Assistant Examiner*—Sean McGarry
*Attorney, Agent, or Firm*—Pioneer Hi-Bred International, Inc.

[57] ABSTRACT

The present invention provides methods for increasing the level of preselected amino acids in seeds of plants, thereby enhancing the nutritional value of the seeds, by genetic modification. The present invention is particularly useful in increasing the methionine, lysine, and/or cysteine content in seeds of plants. Also provided, are isolated endogenous DNA molecules which encode soybean albumins. The present invention also provides an antibody which is capable of specifically binding to soybean albumins. The present invention further provides methods for isolating and purifying 2S albumins.

28 Claims, 6 Drawing Sheets

OTHER PUBLICATIONS

Gamborg, et al.; "Nutrient Requirements of Suspension Cultures of Soybean Root Cells" *Exp. Cell. Res.;* vol. 50; p. 151–158; (1968).

Prosen, et al.; "Transfer of a Ten–Member Genomic Library to Plants using *Agrobacterium tumefaciens*" *Biotechnology;* vol. 5; pp. 966–971; (1987).

Meyer, et al.; "Isolation and Characterization of Monoclonal Antibodies Directed Against Plant Plasma Membrane and Cell Wall Epitopes: Identification of a Monoclonal Antibody that Recognizes Extensin and Analysis of the Process of Epitope Biosynthesis in Plant Tissues and Cell Cultures" *J. Cell. Biol.;* vol. 107; pp. 163–175; (1988).

Nordlee et al., "Investigations of the Allergenicity of Brazil Nut 2S Seed Storage Protein in Transgenic Soybean", Food Safety Evaluation. Proceedings of an OECD–Sponsored Workshop held on 12–15 Sep. 1994, Oxford, UK, pp. 151–155. 16 Ref., 1996.

de Lumen, B.O., "Molecular Approaches to Improving the Nutritional and Functional Properties of Plant Seeds as Food Sources: Developments and Comments", *Journal of Agricultural and Food Chemistry,* vol. 38, No. 9, pp. 1779–1788, Sep. 1990.

George et al, "A Novel Methionine–Rich Protein in Soybean Seed: Identification, Amino Acid Composition, and N–Terminal Sequence", *Journal of Agricultural and Food Chemistry,* vol. 39, No. 1, pp. 224–227, 1991.

Kho et al., "Identification and isolation of methionine–cysteine rich proteins in soybean seed", *Plant Foods for Human Nutrition,* vol. 38, pp. 287–296, 1988.

Odani et al., "Amino Acid Sequence of a Soybean (*Glycine max*) Seed Polypeptide Having a Poly (L–Aspartic Acid) Structure", *The Journal of Biological Chemistry,* vol. 262, No. 22, pp. 10502–10505, 1987.

Beachy et al., "Accumulation and assembly of soybean β–conglycinin in seeds of transformed petunia plants", *Embo Journal,* vol. 4, pp. 3047–3053, 1985.

Utsumi et al., "Synthesis, processing and accumulation of modified glycinins of soybean in the seeds, leaves and stems of transgenic tobacco", *Plant Science,* vol. 92, pp. 191–202, 1993.

Revilleza et al., "An 8 kDa Methionine–Rich Protein from Soybean (*Glycine max*) Cotyledon: Identification, Purification, and N–Terminal Sequence", *Journal of Agricultural and Food Chemistry,* vol. 44, pp. 2930–2935, 1996.

AL1    N-terminal amino acid sequence by Edman degradation

SKWQQHQQES?REQLKGIN                              YIRKKEGKEEEEGHMQK??SEM
    small chain                                       large chain AL2    N-terminal amino acid sequence by Edman degradation SKWFQQHQQES?REQLKGINLNP?E?IM                     YIRKKEGKEEEEGHMQK??SEMSELK
    small chain                                       large chain p9330  (pAL1_42, partial aa sequence deduced from cDNA)
SKWQQHQQESCREQLKGINLNPCEHIMEKIQAGRRGEDGSDEDHILIRTMPGRINYIRKKEGKEEEEGHMQKCCSEMSELKSPI...

AL3    (aa sequence by Edman degradation)

SKWQQHQQDS?RKQLQGVNLSP?EKHIME                    EGKDEDEEEEGHMQK??
    small chain                                       large chain p9331  (pAL1_49, partial aa sequence deduced from cDNA)
SKWQHQQDSCRKQLQGVNLTPCEKHIMEKIQGRGDDDDDDDDDNHILRTMRGRINYIRRNEGKDEDEEEGHMQKCCTEMSELRS...

```
1    GCA CGA GAA ATG ACC AAG CTT ACA ATT CTC ATC GCT CTT CTC TTC
      A   R   E   M   T   K   L   T   I   L   I   A   L   L   F
49   ATC GCC CAC ACC TGC TGC GCC AAG CTC TCC CAA CAG CAG CAA GAG
      I   A   H   T   C   C   A   K   L   S   Q   Q   Q   Q   E
97   AGC TGC CGC GAG CAG CAG ATC CTT TGG GGG ATC CAC CCC TGT GAG CAC
      S   C   R   E   Q   Q   I   L   W   G   I   H   P   C   E   H
145  ATC ATG ATG AAG AAG CAA ATC ATC CTC CAA AAC CTC GGC GAC GCC GAC
      I   M   M   K   K   Q   I   I   L   Q   N   L   G   D   A   D
193  GAA GAT CAC ATT CTC TTG AGG ACC ATG CGC CCG GGA AGA ATC AAC TAC ATC
      E   D   H   I   L   L   R   T   M   R   P   G   R   I   N   Y   I
241  AGG AAG AAG GAA GGA GAA AAG GAA ACC GAG GAA GAA GGA GAA CAC ATG CAG AAG
      R   K   K   E   G   E   K   E   T   E   E   E   G   E   H   M   Q   K
289  TGC AGC GAG ATG CTC AAA AGC GAG CTG AAA CCC AGC ATA TGC CAG TGC AAA
      C   S   E   M   L   K   S   E   L   K   P   S   I   C   Q   C   K
337  GCG CTA CAA ATA ATA AGC CAG CAA AAC CAG CAA ATA CTC GAG GGG AAG
      A   L   Q   I   I   S   Q   Q   N   Q   Q   I   L   E   G   K
385  GAG AAG AAG CAG ATG ATG GAG GAT AAC CTC GAG CTG GCT ATT AGG CGC
      E   K   K   Q   M   M   E   D   N   L   E   L   A   I   R   C
433  AGG TTG GGA CCC ATG ATA GGG AGA AGG TCC TCC GAT GAC GAT TGA AAA
      R   L   G   P   M   I   G   R   R   S   S   D   D   D   *
481  AAA AGT ACT ACT AAC ACA TAT ATG TGT TAG TTT ATG CTA AGA AGA
529  ACG TAT AAG CTA TCT CCG TAT GTT GTA TAT TAA AAA GAT CAT CAC
577  TGG TGA ATG GTG ATC GTG TAT GTA ACG TAG TGG GCA ATG GAA GCA CTT
625  AGA GTG TGC TTT GTG GCC TTG CCC TCT GTT TTG ATA ACT GAG TTT
673  GCG AAT ACC GTT CGT TTT TCC CTT CAA AAA AAA AAA AAA AAA AAA
721  AAA
```

FIG. 3

```
        L   S   V   P   N   R   H   E   K   M   T   K   F   T   I   L
  1   GAG CTC GTG CCG AAT CGG CAC GAG AAA ATG ACC AAG TTC ACA ATC CTC
        L   I   S   L   Q   Q   F   C   I   A   T   C   S   A   S   K
 49   CTC ATC TCT CTT CAG CAA TTC TGC ATC GCC ACT TGC AGC TCC AAA
        W   Q   H   H   P   E   R   L   H   K   Q   Q   S   G   V   N
 97   TGG CAG CAC CAC CCC GAG CGC CTC CAC AAG CAG CAG AGC GGG GTG AAC
        L   T   P   D   K   E   M   L   H   E   K   Q   Q   G   R   G
145   CTC ACG CCC GAT AAG GAG ATG CTC CAC GAG AAG CAA CAG GGC CGC GGC
        D   D   D   D   D   D   N   Y   N   N   E   K   L   R   R   M
193   GAT GAC GAT GAT GAC GAC AAT TAC AAC AAC GAA AAG CTC AGG AGG ATG
        R   G   G   R   A   I   M   H   C   T   A   G   K   D   D   D
241   CGG GGA GGA AGA GCA ATC ATG CAC TGC ACA GCA GGA AAA GAC GAC GAC
        E   E   E   E   P   K   C   Q   C   E   K   T   E   M   S   E
289   GAA GAA GAA GAA CCC AAA TGC CAG TGC GAG AAG ACA GAA ATG AGC GAG
        L   R   S   A   E   E   L   E   E   K   A   Q   C   L   K   E
337   CTG AGA AGC GCC GAA GAG CTG GAG GAG AAA GCG CAG TGC CTG AAG GAG
        N   Q   S   L   N   L   A   M   R   K   F   G   P   I   K   Q
385   AAC CAG AGC CTG AAC CTG GCT ATG AGG AAG TTT GGA CCC ATC AAG CAG
        E   L   I   S   D   D   *
433   GAG CTC ATT TCC GAC GAT GAC TAA GAA GTT AAA AGC AAT GTT GTC ACT
481   TGC GAC TTG TCC TCC GAT GAC TAA CAC ATG ATG TAG TTT ATG CTA AAC
529   TGT ACG TAC TAA CAC ATG ATG TGA TAG TTT ATG CTA AGC TAT AAC
577   ATA AGC TGT CTG TGA GTG TGT TGT ATA TTA ATA AAG ATC ACT GGT
625   GAA TGG TGA TCG TGT ACG TAC CCT ACT TAG TAG GCA ATG GAA GCA CTT
673   AGA GTG TGC TTT GTG CAT GGC CTT GCC TCT GTT TTG AGA CTT TTG TAA
721   TGT TTT CGA GTT TAA ATC TTT GCC TTT GCG GAA AAA AAA AAA AAA AAA
769   AAA AAA AAA
```

FIG. 4

```
  1  GAG CTC GTG CCG AAT CGG CAC GAG AAA ATG ACC AAG TTC ACA ATC CTC
      E   L   V   P   N   R   H   E   K   M   T   K   F   T   I   L
 49  CTC ATC TCT CTT CAG CAA TTC CTC ATC GCC CAC ACT TGC AGC GCC TCC AAA
      L   I   S   L   Q   Q   F   L   I   A   H   T   C   S   A   S   K
 97  TGG CAG CAC CAC TGC TGC AGC CAG AAG CAG AAG CAG AAG GCC GGG GTG
      W   Q   H   H   C   C   S   Q   K   Q   K   Q   K   A   G   V
145  CTC ACG CCC TGC AAG GAG ATG ATC AAG ATG ATG CAC CAC CTT CGC
      L   T   P   C   K   E   M   I   K   M   M   H   H   L   R
193  GAT GAC GAT GAT TAC GAT GAC AAG GAC AAT GAT CAC AAG GAC ATG ACC
      D   D   D   D   Y   D   D   K   D   N   D   H   K   D   M   T
241  CGG GGA AGA ATC AAC TAC ATA CGT AAG AAG GAA GGA AGG GAC GAA GAC
      R   G   R   I   N   Y   I   R   K   K   E   G   R   D   E   D
289  GAA GAA GAA CCC CAG CAG ATG CAG CAG CTG CTG ACA GAA AAA AGC AGC GAG
      E   E   E   P   Q   Q   M   Q   Q   L   L   T   E   K   S   S   E
337  CTT AAG AGC AAA CCC TGC CAG CAG ATC CTG CTG AAG AAG AAG ATG
      L   K   S   K   P   C   Q   Q   I   L   L   K   K   K   M
385  AAC CAG GAG GAA GAG CTG GAG GAG AAC AAG GAG AAG GAG AAG GAG AAG
      N   Q   E   E   E   L   E   E   N   K   E   K   E   K   E   K
433  GAG CTT ATG AAC ACT GCT GAT TTT AGG TGC CCC ATG CCC ATC GGA
      E   L   M   N   T   A   D   F   R   C   P   M   P   I   G
481  TGC GAC TTG TCC TCC GAT GAC TAA TAG ATG *
      C   D   L   S   S   D   D   *   *   M
529  TGT ACG TAC TAA CAC ATG ATG TTT ATG CTA GCT AGC TAT GTC ACT AAC
577  ATA AGC TGT CTC TGA GTG TGT TGT ATA TTA ATA AAG ATC ATC ACT GGT
625  GAA TGG TGA TCG TGT ACG TAC CCT ACT TAG TAG GCA ATG GAA GCA CTT
673  AGA GTG TGC TTT GTG CAT GGC CTT GCC TCT TTG AGA CTT TTG TAA
721  TGT TTT CGA GTT TAA ATC TTT GCC TTT GCG GAA AAA AAA AAA AAA
769  AAA AAA AAA
```

ALTERATION OF AMINO ACID COMPOSITIONS IN SEEDS

BACKGROUND OF THE INVENTION

Feed formulations based on crop plants must typically be supplemented with specific amino acids to provide animals with essential nutrients which are critical to their growth. This supplementation is necessary because, in general, crop plants contain low proportions of several amino acids which are essential for, and cannot be synthesized by, monogastric animals.

The seeds of crop plants contain different classes of seed proteins. The amino acid composition of these seeds reflects the composition of the prevalent classes of proteins. Amino acid limitations are usually due to amino acid deficiencies of these prevalent protein classes.

Among the amino acids necessary for animal nutrition, those that are of limited availability in crop plants include methionine, lysine and cysteine. For example, in soybean, the 7S globulin accounts for about 30% of the seed proteins but contains only 0.3% of methionine, whereas the Bowman-Birk inhibitor ("BBI") accounts for approximately 1% of seed proteins but contains approximately 20% sulfur containing amino acids. Attempts to increase the levels of these amino acids by breeding, mutant selection, and/or changing the composition of the storage proteins accumulated in the seeds of crop plants, have met with limited success, or were accompanied by a loss in yield.

For example, although seeds of corn plants containing a mutant transcription factor, (opaque 2), or a mutant αzein gene, (floury 2), exhibit elevated levels of total and bound lysine, there is an altered seed endosperm structure which is more susceptible to damage and pests. Significant yield losses are also typical.

An alternative means to enhance levels of free amino acids in a crop plant is the modification of amino acid biosynthesis in the plant. The introduction of a feedback-regulation-insensitive dihydrodipicolinic acid synthase ("DHDPS") gene, which encodes an enzyme that catalyzes the first reaction unique to the lysine biosynthetic pathway, into plants has resulted in an increase in the levels of free lysine in the leaves and seeds of those plants. However, these increases are insufficient to significantly increase the total amino acid content of the seed because the level of free amino acid in seeds is, in general, only a minor fraction of the total amino acid content.

The expression of the lysC gene, which encodes a mutant bacterial aspartate kinase that is desensitized to feedback inhibition by lysine and threonine, from a seed-specific promoter in tobacco plants, has resulted in an increase in methionine and threonine biosynthesis in the seeds of those plants. See Karchi, et al.; *The Plant J*.; Vol. 3; p. 721; (1993); incorporated herein in its entirety by reference. However, expression of the lysC gene results in only a 6–7% increase in the level of total threonine or methionine in the seed. Thus, the expression of the lysC gene in seeds has a minimal impact on the nutritional value of those seeds and, thus, supplementation of feed containing lysC transgenic seeds with amino acids, such as methionine and threonine, is still required.

There are additional molecular genetic strategies available for enhancing the amino acid quality of plant proteins. Each involves molecular manipulation of plant genes and the generation of transgenic plants.

Protein sequence modification involves the identification of a gene encoding a major protein, preferably a storage protein, as the target for modification to contain more codons of essential amino acids. A critical task of this approach is to be able to select a region of the protein that can be modified without affecting the overall structure, stability, function, and other cellular and nutritional properties of the protein. The variable region(s) in a polypeptide, as identified through sequence analysis and comparison of related protein species, offer possible target sites for such modifications.

These studies indicate both that it is feasible to increase the essential amino acid residues in a seed protein by sequence modifications, and that it is important to select suitable target sites.

The development of DNA synthesis technology allows the design and synthesis of a gene encoding a new protein with desirable essential amino acid compositions. For example, researchers have synthesized a 292-base pair DNA sequence encoding a polypeptide composed of 80% essential amino acids and used it with the nopaline synthetase (NOS) promoter to construct a chimeric gene. Expression of this gene in the tuber of transgenic potato has resulted in an accumulation of this protein at a level of 0.02% to 0.35% of the total plant protein. This low level accumulation is possibly due to the weak NOS promoter and/or the instability of the new protein.

A protein of minor quantity in a plant may contain elevated levels of an essential amino acid that is limiting. By enhancing the expression of the gene encoding this protein, it may be possible to increase the concentration of this protein, and thus the content of this particular essential amino acid. In this connection, a 10.8-kD putative methionine-rich protein has recently been considered in soybean seeds as a good candidate for improving the protein quality of soybeans.

Additionally, recombinant DNA and plant transformation techniques permit the transfer of genes between diverse plant species. Thus, a gene encoding an essential amino acid-rich protein isolated from a specific plant can be introduced into other plants to enhance their protein quality. Several plant proteins containing unusually high levels of the essential sulfur amino acids and their genes have been identified and isolated. They are prime candidates for use in protein improvement.

Tobacco has been used as a test plant to demonstrate the feasibility of this approach by transferring a chimeric gene containing the bean phaseolin promoter and the cDNA of a sulfur-rich protein Brazil Nut Protein ("BNP"), (18 mol % methionine and 8 mol % cysteine) into tobacco. Amino acid analysis indicates that the methionine content in the transgenic seeds is enhanced by 30% over that of the untransformed seeds. This same chimeric gene has also been transferred into a commercial crop, canola, and similar levels of enhancement were achieved.

However, an adverse effect is that lysine content decreases. Additionally, BNP has been identified as a major food allergen. Thus it is neither practical nor desirable to use BNP to enhance the nutritional value of crop plants.

This finding marks an area that needs further research. It is also useful to point out here that there are advantages and disadvantages to each of these approaches. While the protein sequence modification and the synthetic gene strategies have the flexibility of engineering and designing a gene with desirable essential amino acid composition, they suffer from the possibility of generating unknown structural and biological properties in the protein product. Both the heterologous and homologous gene approaches enjoy the advantage of utilizing naturally-occurring genes. However, the identification of a gene encoding a protein rich in a particular essential amino acid, if it indeed exists, could be a formidable task.

There is therefore a need to change the ratio of protein classes, without detrimental side effects. Endogenous proteins are well adapted for intracellular assembly, targeting and processing. Additionally, a change of the protein composition reduces the possibility of generating unknown risks for human or animal health because all protein compounds are already present in the plant prior to modification. However, some endogenous proteins, such as BBI, which are rich in essential amino acids, are anti-nutritional proteins.

Based on the foregoing, there exists a need to identify endogenous seed storage proteins with increased amounts of essential amino acids, which are present in relatively low amounts in unmodified seeds, to enhance the nutritional value of seeds by genetically modifying the seeds so as to over-express genes encoding these proteins. The genetic modification should not be accompanied by detrimental side effects such as allergenicity, anti-nutritional quality or poor yield.

It is therefore an object of the present invention to provide methods for increasing the nutritional content of feed.

It is a further object of the present invention to provide methods for genetically modifying seeds so as to increase amounts of essential amino acids present in relatively low amounts in unmodified seeds.

It is a further object of the present invention to provide methods for introducing endogenous proteins into seeds.

It is a further object of the present invention to provide methods for increasing the nutritional content of seeds without detrimental side effects such as allergenicity, poor yield or anti-nutritional quality.

SUMMARY OF THE INVENTION

The methods of the present invention comprise the transformation of plant cells by introducing an expression cassette comprising a preselected DNA segment encoding a seed storage protein.

The present invention also provides a fertile transgenic soybean plant containing an isolated preselected DNA segment comprising a promoter and encoding a seed storage protein comprising preselected amino acids under the control of the promoter.

The present invention also provides an isolated and purified DNA molecule comprising a preselected DNA segment encoding a soybean seed storage protein.

The present invention also provides an antibody capable of specifically binding soybean albumin.

The present invention also provides methods of isolating albumins from seeds.

BRIEF DESCRIPTION OF THE FIGURES

FIG. 1 depicts the amino-terminal sequences of albumin 1, albumin 2, and albumin 3, as determined by Edman degradation of proteins isolated from PVDF blots.

FIG. 2 depicts the cDNA sequence (SEQ ID NO: 1) of albumin 1 isolated from a soybean seed cDNA library, and the corresponding predicted amino acid sequence of albumin 1 (SEQ ID NO: 2).

FIG. 3 depicts the cDNA sequence (SEQ ID NO: 3) of albumin 3 isolated from a soybean seed cDNA library, and the corresponding predicted amino acid sequence of albumin 3 (SEQ ID NO: 4).

FIG. 4 depicts the cDNA sequence (SEQ ID NO: 5) and the amino acid sequence (SEQ ID NO: 6) of a chimeric albumin which comprises sequences from albumin 1 and albumin 3.

DETAILED DESCRIPTION OF THE INVENTION

Figure 5:
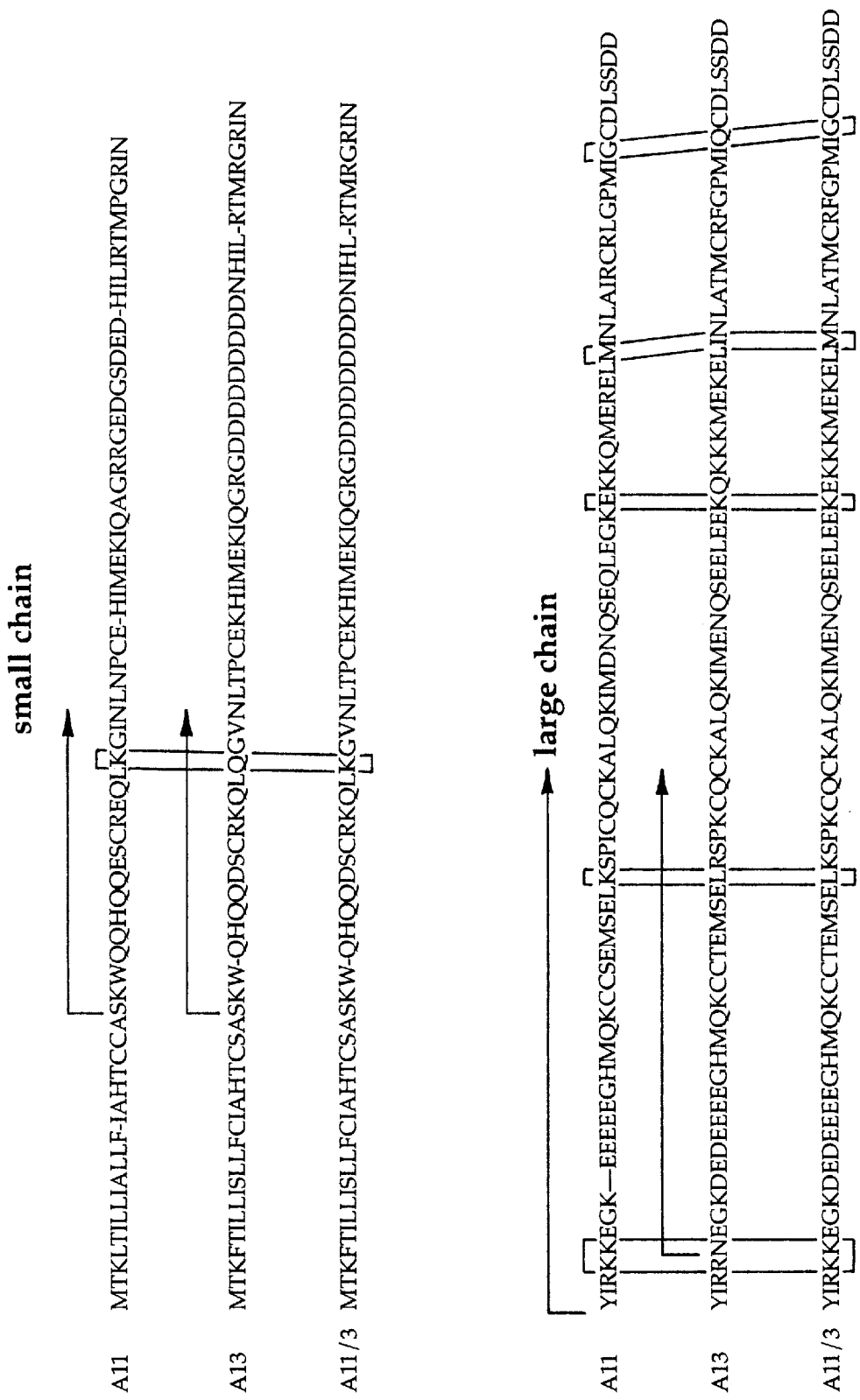
FIG. 5 termed albumin 1/3 depicts a comparison of the amino acid sequences of albumin 1, albumin 3 and albumin 1/3.

The present invention provides a method for genetically modifying seeds to increase the level of at least one preselected amino acid in the seed so as to enhance the nutritional value of the seeds. The methods comprise the introduction of an expression cassette into regenerable plant cells to yield transformed plant cells. The expression cassette comprises a preselected DNA segment, encoding a soybean seed storage protein comprising preselected amino acids, operably linked to a promoter functional in plant cells.

A fertile transgenic plant is regenerated from the transformed cells, and seeds are isolated from the plant. The seeds comprise the protein which is encoded by the preselected DNA segment and which is produced in an amount sufficient to increase the amount of the preselected amino acid in the seeds of the transformed plants, relative to the amount of the preselected amino acid in the seeds of a corresponding untransformed plant, e.g., the seeds of a regenerated control plant that is not transformed or corresponding untransformed seeds isolated from the transformed plant.

Preferably, the preselected amino acid is lysine. More preferably, there is an additional preselected amino acid. Even more preferably, the additional preselected amino acid is cysteine or methionine.

A preferred embodiment of the present invention is the introduction of an expression cassette into regenerable soybean cells. Also preferred is the introduction of an expression cassette comprising a preselected DNA segment encoding an endogenous polypeptide sequence.

The present invention encompasses segments having sufficient similarity to the segments disclosed hereinafter. Generally, such sufficient similarity should comprise at least about 60% identity or 60% homology between base pairs 10 through 474 in albumin 1 (SEQ ID NO: 1), between base pairs 28 through 501 in albumin 3 (SEQ ID NO: 3) and between base pairs 28 and 501 in albumin 1/3 (SEQ ID NO: 5). Preferably, such sufficient similarity should comprise at least about 70% identity or 70% homology. More preferably, such sufficient similarity should comprise at least about 80% identity or 80% homology. Even more preferably, such sufficient similarity should comprise at least about 90% identity or 90% homology. Most preferably, the segments of the present invention are of the sequences disclosed in SEQ ID NO: 1, SEQ ID NO: 3 and SEQ ID NO: 5 respectively.

The present invention also encompasses variations in the sequences described above, wherein such variations are due to site-directed mutagenesis, or other mechanisms known in the art, to increase or decrease levels of selected amino acids of interest. For example, site-directed mutagenesis to increase levels of lysine, methionine and/or cysteine, and/or to decrease levels of asparagine and/or glutamine is a preferred embodiment.

The present invention also provides a fertile transgenic plant. The fertile transgenic plant contains an isolated preselected DNA segment comprising a promoter and encoding a seed storage protein comprising preselected amino acids under the control of the promoter. The DNA segment is expressed as the seed storage protein so that the level of preselected seed storage protein amino acids in the seeds of the transgenic plant is increased above the level in the seeds of a plant which only differ from the seeds of the transgenic plant in that the DNA segment or the encoded seed protein is under the control of a different promoter. The DNA segment is transmitted through a complete normal sexual cycle of the transgenic plant to the next generation.

Also provided is an isolated and purified DNA molecule comprising a preselected DNA segment encoding a soybean seed storage protein. A most preferred embodiment of the invention is a preselected DNA segment encoding a soybean albumin. See e.g. Shewry, et al.; *The Plant Cell*; Vol. 7; No. 7; pp. 945–956; (1995); incorporated herein in its entirety by reference.

The present invention also provides an expression cassette comprising a preselected DNA segment encoding a soybean seed storage protein, operably linked to a promoter functional in a host cell. Preferred promoters useful in the practice of the invention are those seed-specific promoters that allow expression of the preselected DNA segment selectively in seeds to avoid any potential deleterious effects associated with the expression of the preselected DNA segment in non-seed organs.

Other embodiments of the invention include plants, plant parts, seeds and microorganisms transformed with the preselected DNA segment encoding a seed storage protein. Preferably, the seed storage protein is an albumin. More preferably, the seed storage protein is a soybean albumin.

Other embodiments of the present invention also include a chimera with increased levels of preselected amino acids.

In a preferred embodiment of the present invention, a method is provided for the simple, rapid, and reliable production of transgenic soybean plants with increased accumulation of lysine, in the seeds produced thereby. In a more preferred embodiment, increased accumulation of methionine and/or cysteine occurs in addition to increased accumulation of lysine. The method is genotype-independent and shows a substantial, unexpected improvement over previously used systems.

The present invention also provides methods for isolating and purifying 2S albumins comprising the separation of albumins from contaminants by specifically interacting the albumins with the matrix of a carbohydrate resin, preferably a dextran resin, even more preferably Sephadex G25. The above methods for isolation and purification are unexpected given the molecular sieve characteristics of the resin. The specific interaction between the albumins and the matrix has applications useful for batch processes.

As used herein, a "preselected DNA segment" means an exogenous or recombinant DNA sequence or segment that encodes a soybean seed storage protein, wherein the seed storage protein is preferably not a functional protease inhibitor, not a functional a amylase inhibitor and not a lectin.

A preferred seed storage protein of the invention is one that has an increased content of lysine as well as sulfur containing amino acids, i.e., methionine and/or cysteine. The choice of the preselected DNA segment and amino acid is based on the amino acid composition of the protein encoded by the preselected DNA segment, and the ability of the protein to accumulate in seeds. Moreover, the amino acid composition of the protein can be manipulated by methods, such as site-directed mutagenesis of the preselected DNA segment encoding the protein, so as to result in expression of a protein that is increased in the amount, i.e., content, of a particular amino acid. A preferred embodiment of the invention is a preselected DNA segment encoding a soybean seed storage protein that has an elevated amount of lysine, and methionine and/or cysteine, such as a preselected DNA segment encoding a soybean albumin. Because an endogenous protein is utilized, the possibility of generating unknown risks for human and/or animal health is reduced.

As used herein, the term "high lysine content protein" means that the protein has at least about 7% lysine, more preferably at least about 10% lysine, even more preferably at least about 12% lysine, and most preferably at least about 13% lysine. In a preferred embodiment, the high lysine content protein is also a high sulfur content protein.

As used herein, the term "high sulfur content protein" means that the protein contains methionine and/or cysteine in addition to lysine, at levels indicated hereinafter. The high sulfur content protein has at least about 6% methionine and/or cysteine, preferably at least about 9% methionine and/or cysteine, and more preferably at least about 11% methionine and/or cysteine.

As used herein, "increased" or "elevated" levels or amounts of preselected amino acids in a transformed plant are levels which are greater than the levels or amounts in the corresponding untransformed plant. For example, the average methionine content in soybean seed proteins is about 1.4%, the average cysteine content in soybean seed proteins is about 1.4%, and the average lysine content in soybean seed proteins is about 6.0% (George, et al.; *J. Agric. Food Chem.*; Vol. 34; p. 224; (1991); incorporated herein in its entirety by reference). Thus, the expression of soybean albumin 1 having SEQ ID NO: 2, which has about 12% of a combination of methionine and cysteine and about 10% lysine, in seeds results in an increase in the level or amount of methionine, cysteine and lysine in those seeds. Furthermore, the expression of soybean albumin 3, having SEQ ID NO: 4, which has about 12% of a combination of methionine and cysteine and about 10% lysine, in seeds results in an increase in the level or amount of methionine, cysteine and lysine in those seeds. The amino acid composition of a protein can be determined by methods well known to the art.

Increased amounts of preselected amino acids other than lysine in a transformed plant are preferably at least about 15 to 30%, preferably at least about 30 to 50%, and most preferably about 50 to 100%, greater than the amounts of the preselected amino acid in a non-transformed plant. Increased amounts of preselected lysine in a transformed plant are preferably at least about 5–10%, more preferably at least about 10–15%, even more preferably at least about 15–25%, most preferably at least about 25–50% greater than the amounts of lysine in a non-transformed plant.

As used herein, "genetically modified plant" means a plant which comprises a preselected DNA segment which is introduced into the genome of the plant by transformation. The term "wild type" refers to an untransformed plant i.e., one where the genome has not been altered by the introduction of the preselected DNA segment.

As used herein, "plant" includes but is not limited to plant cells, plant tissue and plant seeds. For the present invention, preferred plants include soybean, canola, sunflower, sorghum and corn. More preferred plants include soybean and corn. The most preferred plant is soybean.

As used herein with respect to a preselected DNA segment encoding a protein, the term "expresses" means that the preselected DNA segment is incorporated into the genome of the cells, so that the product encoded by the preselected DNA segment, e.g., a sulfur-rich protein such as albumin, is produced within the cells. For example, novel plants resulting from expression of a preselected DNA segment encoding an albumin contain extractable levels of the albumin of at least about 3%, preferably at least about 5%, more preferably at least about 10%, and even more preferably at least about 20%, of the total protein in the seed.

The class of plants which can be used in the method of the invention is generally as broad as the class of seed-bearing higher plants amenable to transformation techniques, including both monocotyledonous and dicotyledonous plants. Seeds derived from plants regenerated from transformed plant cells, plant parts or plant tissues, or progeny derived from the regenerated transformed plants, may be used directly as feed or food, or further processing may occur. In the practice of the present invention, the most preferred plant seed is selected from that of soybean, canola, sunflower, sorghum and corn. More preferably, the plant seed is that of corn or soybean, most preferably that of the soybean *Glycine max*. The transformation of the plants in accordance with the invention may be carried out in essentially any of the various ways known to those skilled in the art of plant molecular biology. These include, but are not limited to, microprojectile bombardment, microinjection, electroporation of protoplasts or cells comprising partial cell walls, and Agrobacterium-mediated DNA transfer.

As used herein, "recombinant" DNA is a DNA sequence or segment that has been isolated from a cell, purified, or amplified.

As used herein, "isolated" means either physically isolated from the cell or synthesized in vitro on the basis of the sequence of an isolated DNA segment.

As used herein, "albumin" means a seed protein whose genes encode peptide precursors similar in organization to and homologous to the 2S albumin seed protein family. See Shewry supra; incorporated herein in its entirely by reference.

As used herein, "2S soybean albumin" means a Glycine seed protein whose genes encode peptide precursors which are homologs of the albumins.

The present invention provides for the expression of a protein of preselected amino acid composition in a seed at levels sufficient to reduce or obviate feed supplementation. A preferred protein, which is encoded by a preselected DNA segment of the invention, is a seed storage protein. Because seed storage proteins normally accumulate in seed, overexpression of these proteins in seed will not have to overcome incompatibility with the assembly, targeting and processing mechanisms in the cell. In addition, there is minimal risk of enhancement of induction of allergenic reactions in comparison with wild type seeds. A preferred embodiment of the invention includes a seed storage protein rich in lysine as well as sulfur-containing amino acids. One example of such a protein is an albumin. To enhance expression of a protein of preselected amino acid composition in a seed at a level to increase the level of the preselected amino acid in the seed, expression cassettes with seed-specific promoters can be employed.

I. DNA Used for Transformation

DNA-encoding seed storage protein(s) useful for introduction into plant cells includes DNA that has been derived or isolated from any source, that may be subsequently characterized as to structure, size and/or function, chemically altered, and later introduced into the plant. An example of DNA "derived" from a source, would be a DNA sequence or segment that is identified as a useful fragment within a given organism, and which is then synthesized in essentially pure form. An example of such DNA "isolated" from a source would be a useful DNA sequence that is excised or removed from the source by chemical means, e.g., by the use of restriction endonucleases, so that it can be further manipulated, e.g., amplified, for use in the invention, by the methodology of genetic engineering.

Therefore, useful DNA includes completely synthetic DNA, semi-synthetic DNA, DNA isolated from biological sources, and DNA derived from RNA. The DNA isolated from biological sources, or DNA derived from RNA, includes, but is not limited to, DNA or RNA from plant genes, and non-plant genes such as those from bacteria, yeasts, animals or viruses. The DNA or RNA can include modified genes, portions of genes, or chimeric genes, including genes form the same or different genotype. The term "chimeric gene" or "chimeric DNA" is defined as a gene or DNA sequence or segment comprising at least two DNA sequences or segments from species which do not recombine DNA under natural conditions, or which DNA sequences or segments are positioned or linked in a manner which does not normally occur in the native genome of untransformed plant. Thus, it is within the scope of the invention to isolate a preselected DNA segment from a given soybean genotype, and to subsequently introduce at least one copy of the preselected DNA segment into the same genotype.

A preselected DNA segment of the invention can be identified by standard methods, e.g., enrichment protocols, or probes, directed to the isolation of particular nucleotide or amino acid sequences. The preselected DNA segment can be identified by obtaining and/or screening of a DNA or cDNA library generated from nucleic acid derived from a particular cell type, cell line, primary cells, or tissue. Screening for DNA fragments that encode all or a portion of the preselected DNA segment can be accomplished by screening plaques from a genomic or cDNA library for hybridization to a probe of the preselected DNA segment from other organisms or by screening plaques from a cDNA expression library for binding to antibodies that specifically recognize the protein encoded by the preselected DNA segment. DNA fragments that hybridize to a preselected DNA segment probe from other organisms and/or plaques carrying DNA fragments that are immunoreactive with antibodies to the protein encoded by the preselected DNA segment can be subcloned into a vector and sequenced and/or used as probes to identify other cDNA or genomic sequences encoding all or a portion of the preselected DNA segment.

Portions of the genomic copy or copies of the preselected DNA segment can be partially sequenced and identified by standard methods including either DNA sequence homology to other homologous genes or by comparison of encoded amino acid sequences to known protein sequences. Once portions of the preselected DNA segment are identified, complete copies of the preselected DNA segment can be obtained by standard methods, including cloning or polymerase chain reaction (PCR) synthesis using oligonucleotide primers complementary to the preselected DNA segment. The presence of an isolated full-length copy of the preselected DNA segment can be verified by comparison of its deduced amino acid sequence with the amino acid sequence of native polypeptide sequences.

The preselected DNA segment encoding the seed storage protein can be modified to increase the content of particular amino acid residues in that protein by methods well known to the art, including, but not limited to, site-directed mutagenesis. Thus, derivatives of naturally occurring proteins can be made by nucleotide substitution of the preselected DNA segment encoding that protein so as to result in a protein having a different amino acid at the position in the protein which corresponds to the codon with the nucleotide substitution. The introduction of multiple amino acid changes in a protein can result in a protein which is significantly enriched in a preselected amino acid.

The present invention thus provides a DNA molecule comprising a preselected DNA segment encoding a seed storage protein. The preselected DNA segment can encode any seed storage protein including, but not limited to, the 2S, 7S and 11S seed storage proteins, with or without modification of the sequence encoding those proteins. The skilled artisan will recognize that the choice of the protein encoded by the preselected DNA segment will be based on the amino acid composition of the protein and its ability to accumulate in seeds. The amino acid can be chosen for its nutritional value to produce a value-added trait to the plant or plant part. Amino acids desirable for value-added traits, as well as a source to limit synthesis of an endogenous protein include, but are not limited to, methionine, cysteine, and lysine.

Also provided are methods for increasing the level of at least one preselected amino acid in seeds by expressing a preselected DNA segment encoding a protein in seeds. Preferably, the preselected amino acid is lysine. More preferably, a second preselected amino acid is also included in the present invention. Even more preferably, the second preselected amino acid is methionine or cysteine. Expression of the preselected DNA segment, or multiple copies of the preselected DNA segment, can increase the level of the protein encoded by the preselected DNA segment in the seeds and, thus, the level of the preselected amino acid which has been incorporated into the protein encoded by the preselected DNA segment. Methods and compositions are provided for producing plant cultures, plant tissues, plants and seeds that comprise an expression cassette comprising a preselected DNA segment encoding a protein. The present invention provides a method of genetically engineering plants so that the plants produce seeds with increased levels of at least one preselected amino acid, such that plants and seeds can sexually transmit this trait to their progeny.

In a preferred embodiment, the protein encoded by the preselected DNA segment is a sulfur rich 2S seed storage protein, such as albumin. In a more preferred embodiment of the invention, the preselected DNA segment encodes an endogenous 2S soybean albumin. By way of example, and not limitation, those skilled in the art will readily appreciate that the 2S albumin gene from other organisms may be substituted for the soybean 2S albumin protein. See, for example, Coulter, et al.; *J. Exp. Bot.*; Vol. 41; p. 1541; (1990); incorporated herein in its entirety by reference.

Other examples of sulfur-rich plant proteins within the scope of the invention include plant proteins enriched in cysteine but not methionine, such as the wheat endosperm purothionine (Mak and Jones; *Can. J. Biochem.*; Vol. 22; p. 83J; (1976); incorporated herein in its entirety by reference), and the pea low molecular weight albumins (Higgins, et al.; *J. Biol. Chem.*; Vol. 261; p. 11124; (1986); incorporated herein in its entirety by reference). Such proteins also include methionine-rich plant proteins such as from sunflower seed (Lilley, et al.; In: *Proceedings of the World Congress on Vegetable Protein Utilization in Human Foods and Animal Feedstuffs*; Applewhite, H. (ed.); American Oil Chemists Soc.; Champaign, Ill.; pp. 497–502; (1989); incorporated herein in its entirety by reference), corn (Pedersen, et al.; *J. Biol. Chem.* p. 261; p. 6279; (1986); Kirihara, et al.; *Gene*, Vol. 71; p. 359; (1988); both incorporated herein in its entirety by reference), and rice (Musumura, et al.; *Plant Mol. Biol.*; Vol. 12; p. 123; (1989); incorporated herein in its entirety by reference).

Expression Cassettes and Expression Vectors

According to the present invention, a preselected DNA segment encoding a protein, such as a seed storage protein, is identified, isolated, and combined with at least a promoter functional in a host cell, e.g., a plant cell, to provide a recombinant expression cassette. The construction of such expression cassettes which may be employed in conjunction with the present invention are well known to those of skill in the art in light of the present disclosure. See, e.g., Sambrook, et al.; *Molecular Cloning: A Laboratory Manual*; Cold Spring Harbor, N.Y.; (1989); Gelvin, et al.; *Plant Molecular Biology Manual*; (1990); *Plant Biotechnology: Commercial Prospects and Problems*, eds Prakash, et al.; Oxford & IBH Publishing Co.; New Delhi, India; (1993); and Heslot, et al.; *Molecular Biology and Genetic Engineering of Yeasts*; CRC Press, Inc., USA; (1992); each incorporated herein in its entirety by reference.

Promoters

Preferred expression cassettes of the invention will generally include, but are not limited to, a seed-specific promoter. Examples of seed-specific promoters include promoters of seed storage proteins which express these proteins in seeds in a highly regulated manner (Thompson, et al.; *BioEssays*; Vol. 10; p. 108; (1989); incorporated herein in its entirety by reference), such as, for dicotyledonous plants, a bean β-phaseolin promoter, a napin promoter, a β-conglycinin promoter, and a soybean lectin promoter. For monocotyledonous plants, promoters useful in the practice of the invention include, but are not limited to, a maize 15 kD zein promoter, a 22 kD zein promoter, a γ-zein promoter, a waxy promoter, a shrunken 1 promoter, a globulin 1 promoter, and the shrunken 2 promoter. However, other promoters useful in the practice of the invention are known to those of skill in the art.

II. Delivery of DNA to Cells

The expression cassette or vector can be introduced into prokaryotic or eukaryotic cells by currently available methods. For example, the expression cassette or vector can be introduced into plant cells by methods including, but not limited to, Agrobacterium-mediated transformation, electroporation, microprojectile bombardment, microinjection, infectious viruses or viroids, the use of liposomes and the like, all in accordance with well-known procedures. Plant cells useful for transformation include cells cultured in suspension cultures, callus, embryos, meristem tissue, pollen, and the like. Transformed cells can be selected typically using a selectable or screenable marker encoded on the expression vector.

Introduction and expression of foreign genes in dicotyledonous plants such as soybean, tobacco, potato and alfalfa has been shown to be possible using the T-DNA of the tumor-inducing (Ti) plasmid of *Agrobacterium tumefaciens*. Using recombinant DNA techniques and bacterial genetics, a wide variety of foreign DNAs can be inserted into T-DNA in Agrobacterium. Following infection by the bacterium containing the recombinant Ti plasmid, the foreign DNA is inserted into the host of plant chromosomes, thus producing a genetically engineered cell and eventually a genetically engineered plant. A second approach is to introduce root-inducing (Ri) plasmids as the gene vectors.

While Agrobacterium appear to preferably attack dicots, many important crop plants including maize, wheat, rice, barley, oats, sorghum, millet, and rye are monocots and are not known to be easily susceptible to transformation by Agrobacterium. The Ti plasmid, however, may be manipulated in the future to act as a vector for monocot plants. Additionally, using the Ti plasmid as a model system, it may be possible to artificially construct transformation vectors for monocot plants. Ti-plasmids might also be introduced into monocots by artificial methods such as microinjection, or fusion between monocot protoplasts and bacterial spheroplasts containing the T-region, which can then be integrated into the plant nuclear DNA. Other transformation methods are readily available to those skilled in the art.

III. Regeneration and Analysis of Transformants

Following transformation, regeneration is involved to obtain a whole plant from transformed cells and the presence of preselected DNA segment(s) or "transgene(s)" in the regenerating plant detected by assays. The seed derived from the plant is then tested for levels of preselected amino acids. Depending on the type of plant and the level of gene expression, introduction of the preselected DNA segment into the plant can enhance the level of preselected amino acids in an amount useful to supplement the nutritional quality of those seeds.

Techniques for regenerating plants from tissue culture, such as transformed protoplasts or callus cell lines, are known in the art. For example, see Phillips, et al.; *Plant Cell Tissue Organ Culture*; Vol. 1; p. 123; (1981); Patterson, et al.; *Plant Sci.*; Vol. 42; p. 125; (1985); Wright, et al.; *Plant Cell Reports*; Vol. 6; p. 83; (1987); and Barwale, et al.; *Planta*; Vol. 167; p. 473; (1986); each incorporated herein in its entirety by reference. The selection of an appropriate method is within the skill of the art.

Examples of the practice of present invention detailed herein relate specifically to soybean plants and expression vectors operable in dicots. However, the present invention is also applicable to other plants. The expression vectors utilized herein are demonstrably capable of operation in cells of many dicotyledonous plants both in tissue culture and in whole plants. The invention disclosed herein is thus operable in dicotyledonous species to transform individual plant cells and to achieve full, intact plants in dicot plant species which can be regenerated from transformed plant cells and which express preselected seed storage proteins.

The introduced preselected DNA segments are expressed in the transformed plant cells and stably transmitted (somatically and sexually) to the next generation of cells produced. The vector should be capable of introducing, maintaining, and expressing a preselected DNA segment in plant cells. Additionally, it is possible to introduce the vector into a wide variety of cells of plants. The preselected DNA segment is passed on to progeny by normal sexual transmission.

To confirm the presence of the preselected DNA segment (s) or "transgene(s)" in the regenerating plants, or seeds or progeny derived from the regenerated plant, a variety of assays may be performed. Such assays include, for example, "molecular biological" assays well known to those of skill in the art, such as Southern and Northern blotting and PCR; "biochemical" assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently, the expression of a gene product is determined by evaluating the phenotypic results of its expression. These assays also may take many forms, including but not limited to, analyzing changes in the chemical composition, morphology, or physiological properties of the plant. Chemical composition may be altered by expression of preselected DNA segments encoding storage proteins which change amino acid composition and may be detected by amino acid analysis.

Breeding techniques useful in the present invention are well known in the art.

The present invention has been described with reference to various specific and preferred embodiments and will be further described by reference to the following detailed examples. It is understood, however, that there are many extensions, variations, and modifications on the basic theme of the present invention beyond that shown in the examples and description, which are within the spirit and scope of the present invention.

EXAMPLE 1

Isolation and Characterization of Soybean 2S Albumins

Soybean plants (G. max Merr.) varieties are grown in the greenhouse or in the field. If not otherwise stated, reagents and laboratory supplies are obtained from Sigma Chemical Co. (St. Louis, Mo.) or Baxter (McGaw Park, Ill.). Protein concentrations are estimated either according to Bradford (BioRad® protein assay, BioRad®, Hercules, Calif.) or with a modified Lowry assay (DC protein assay, BioRad®) with bovine serum albumin (Pierce, Rockford, Ill.) as a standard.

The present method comprises the steps of:
a) protein extraction from soybean meal;
b) size exclusion chromatography of the protein extract;
c) collection of albumin-containing fractions;
d) separation of albumins from other protein contaminants by specifically interacting the albumins to the matrix of a resin; and
e) ion-exchange chromatography to separate the individual albumins.

SDS polyacrylamide gel electrophoresis ("PAGE") is performed using the Tris-Tricine buffer system developed by Schagger and von Jagow. See Schagger, H. and von Jagow, G., Anal. Biochem. Vol. 166, p. 368 (1987); incorporated herein in its entirety by reference. For routine purposes polypeptides are separated in 16.5% Mini-Protein II precast mini-gels (80×73 mm Ready Gels, BioRad®, Richmond, Calif.) or, when a superior resolution of polypeptides in the molecular weight range between 2 and 25 kDa is required, in 170×150 mm 8–22% polyacrylamide gradient gel using a Model V16 electrophoresis apparatus (GibcoBRL®, Gaithersburg, Md.). Protein bands are detected by staining with Coomassie brilliant Blue R 250.

When indicated, after electrophoretically separating the proteins, the separated polypeptides are electrotransferred to polyvinylidene difluoride (PVDF) membranes (Immobilon PSQ®, Millipore, Bedford, Mass.) using a semi-dry electroblotter (SemiPhor® TE70, Hoefer, San Francisco, Calif.) as described by Matsudaira (J. Biol. Chem.; Vol. 262; p. 10035; (1987); incorporated herein in its entirety by reference). Several precautions are undertaken to prevent blocking of N-terminal amino groups and to minimize modifications of amino acid side chains prior to amino acid sequencing. The Tris/Tricine gels, including the stacking gel, are cast 3–7 days prior to the protein separation and stored sealed at 4° C. Immediately before separation, gels are pre-run at 2V/cm for 15 hours with 0.1% SDS, 0.75M Tris/HCl, pH 8.45 (anode buffer) and 0.1% SDS, 1M Tris/HCl, pH 8.45 (cathode buffer). Following electrotransfer of polypeptides to PVDF (see above) and staining with Coomassie Blue, the blots are washed extensively with water and dried. Polypeptide bands of interest are carefully excised from the membranes and stored in microcentrifuge tubes at 4° C. until needed. N-terminal sequence is obtained from Immobilon PSQ membranes by using an Applied Biosystems 477A Protein sequencer in the Protein Analysis Laboratory of the University of Iowa (Iowa City, Iowa).

Amino acid analysis is carried out on a Beckman 6300 analyzer according to standard procedures. Methionine and cysteine are determined as methionine sulfone and cysteic acid after performic acid oxidation. Isoelectric focusing of proteins is performed in pre-cast slab gels (pH performance range 3.5–6.5, Novex, San Diego, Calif.) with Novex Low Range IEF protein standards according to the manufacturer's recommendations.

To determine whether an isolated protein contains N-linked glycans, Concanavalin A-horseradish peroxidase staining of protein blots (see above) is carried out as described by Faye and Chrispeels (Anal. Biochem.; Vol. 149, p. 218; (1985); incorporated herein in its entirety by reference) with the modification that horseradish peroxidase activity is visualized by chemiluminescence (ECL kit, Amersham, Arlington Heights, Ill.).

For N-Glycosidase F (Boehringer Mannheim, Indianapolis, Ind.) treatment (0.1 U/10 µl, 15 hours at 37° C.) protein samples (10 µg/10 µl) are denatured by 2 min. at 95° C. in 0.1% SDS, 200 mM NaCl, 20 mM Tris/HCl, pH 8.5, cooled to 4° C., supplemented to 1% Triton X-100 and incubated for 15 min. at room temperature prior to enzyme addition.

Purification and Characterization of Lysine-rich and Sulfur-rich Soybean 2S Albumins Transgenic soybean seed expressing a methionine-rich 2S seed storage protein from Brazil Nut (Bertholletia excelsa) ("BNP") shows a reduction in the levels of the sulfur-rich endogenous Bowman-Birk inhibitor (Kollipara, K. P. and Hymowitz, R.; J. Agri. Food; Vol. 40; pp. 2356–2363; (1992); incorporated herein in its entirety by reference) and the reduction of an unknown 14 kDa protein. To determine whether the unknown 14 kDa protein is a methionine-rich seed storage protein, seed proteins from wild type seeds and BNP transgenic seeds are electrophoretically separated and electrotransferred to PVDF membranes, and then the membranes are probed with iodo[$^{14}$C]acetic acid (ICN Radiochemicals, Irvine, Calif.), pH 2.0, according to the method of de Lumen and Kho (J. Agric. Food Chem.; Vol. 35; p. 688; (1987); incorporated herein in its entirety by reference). An autoradiogram of this gel blot shows that the 14 kDa protein is a methionine-rich protein. This protein may belong to a family of methionine-containing peptides previously observed by Kho and de Lumen (Plant Food Hum. Nutr.; Vol. 38; p. 287; (1988); incorporated herein in its entirety by reference) using the same technique.

To purify this protein, mature dry seed of soybean (Glycine max) is ground into a fine meal, defatted by extraction with hexane (1:1 w/v) and vacuum dried. 100 g of defatted flour is homogenized in a Waring blender for 5 min. at 4° C. with 400 ml 10% DMSO, 0.5% n-butanol, 100 mM KCL, 83 mM sodium acetate buffer, pH 5.2, (albumin extraction buffer). All following steps are carried out either on ice or at 4° C.

The slurry is filtered through Miracloth® (Calbiochem, LaJolla, Calif.) and centrifuged at 6000×g for 15 min. The recovered supernatant is dialyzed (Spectra/por 7, MWCO 3500, Baxter, McGaw Park, Ill.) extensively against 0.5% n-butanol, 100 mM KCL, 83 mM sodium acetate buffer, pH 5.2 and concentrated in the dialysis bags to about 100 ml with dry polyethyleneglycol (PEG 8000). Precipitated contaminating globulin proteins are removed by centrifugation at 6000×g for 15 min. and by filtration through a 0.45 µm membrane. The resulting albumin extract contains approximately 20% of the total seed protein. 5–10% of the albumin fraction is represented by the 14 kDa polypeptides which comprises approx. 1–2% of the total soybean seed protein (0.5–1% of the seed weight) in wild-type seeds. The extractability in dilute acidic buffer classifies the 14 kDa proteins as albumins (Osborne, The Vegetable Proteins, Longman, G. (ed.), London (1924); incorporated herein in its entirety by reference). The 14 kDa protein dissociates in SDS PAGE under reducing conditions into two polypeptides, apparently of 10 kDa and of 5 kDa respectively, indicating linkage by disulfide bridges in the holoprotein.

Five ml of the concentrated albumin extract (conc. approx. 20 mg/ml), is further fractionated using an Superdex 75 HiLoad 26/60 column (Pharmacia, Uppsala, Sweden) which is run with the extraction buffer. The flow rate is maintained at 1 ml/min. and fractions of 4 ml are collected and analyzed by PAGE. The fractions containing the putative albumin (fraction 33–35, 18 mg protein), obtained with approximately 50% purity and Kunitz trypsin inhibitor (KTI) (Kollipara supra) as the major contaminant, are adjusted to pH 8.5 with Tris HCl (1M) and chromatographed using a 100 ml Sephadex G 25 sf column (Pharmacia, Uppsala, Sweden) with 50 mM sodium acetate, pH 5.2, running buffer at 1 ml/min.

The 14 kDa proteins exhibit, under these conditions, an unexpected interaction with the dextran matrix of the column and separate from its protein contaminants as a single peak with more than 95% purity. A similar specific interaction with the dextran matrix can be observed with the 2S albumin from Brazil Nut and can be used for its purification in a single step. Other albumins also behave in a similar manner. Other carbohydrate matrices known to the skilled artisan may similarly be used in the process. Though the above mentioned chromatography step has been specifically described, it can be replaced by other techniques involving specific interactions, e.g., but not limited to batch processes.

The above-obtained putative albumin fraction is dialyzed (Spectra/por 7) for 15 hours against 20 mM Tris/HCl pH 8.5 and concentrated in the dialysis bags to about 0.5 mg/ml protein with dry PEG 8000. 5 mg of the desalted protein is filtered through a 0.2 μm membrane filter and fractionated further by ion-exchange chromatography using a MonoQ HR 5/5 (Pharmacia, Uppsala, Sweden) column, developed in a gradient of 0–750 mM NaCl in 20 mM Tris/HCl, pH 8.5 buffer. Three separate peaks, elute at 180 mM NaCl (designated albumin 1), 250 mM NaCl (designated albumin 2), and 360 mM NaCl (designated albumin 3). Albumin 3 (Al3) appears to be the major form, i.e. it contains more than 90% of the protein in all three fractions combined, whereas albumin 1 (Al1) and albumin 2 (Al2) are found to be each approximately 20 times less abundant among the soybean seed proteins when compared to Al 3. All three albumin fractions are obtained at near homogeneity based on SDS-PAGE. After treatment with the reducing agent 2-mercaptoethanol, each of the three albumin forms dissociated in SDS PAGE into two smaller polypeptides of different length, indicating the presence of disulfide bonds in the native protein. The sizes of the larger peptides in each of the reduced albumins appear to be similar (10 kDa), whereas the shorter peptides appear to be of different sizes. The Al1 small chain has an estimated molecular weight of 4.5 kDa, the Al2 small chain of 4.8 kDa and the Al3 small chain of 5.1 kDa, respectively.

PVDF blots of the electrophoretically separated Al2 large chain, Al2 small chain, Al3 large chain and Al3 short chain are subjected to amino acid analysis (Table 1). Both albumins contain the predicted high contents of methionine and in addition, a surprisingly high percentage of lysine. Although it appears that the amino acid compositions of the two albumins are generally similar, some clear differences with some amino acids are observed.

TABLE 1

AMINO ACID COMPOSITION

| | A12 | | A13 | |
| --- | --- | --- | --- | --- |
| | 5 kDa Peptide Mole % | 11 kDa Peptide Mole % | 5 kDa Peptide Mole % | 11 kDa Peptide Mole % |
| Cys | 1.93 | 3.38 | 2.79 | 2.88 |
| Asx | 10.89 | 8.17 | 17.96 | 9.47 |
| Met | 3.13 | 8.00 | 2.35 | 8.70 |
| Thr | 1.76 | 1.03 | 4.10 | 3.02 |
| Ser | 9.62 | 9.00 | 7.05 | 7.43 |
| Glx | 21.86 | 19.39 | 15.42 | 21.80 |
| Pro | 0.00 | 2.65 | 3.67 | 3.02 |
| Gly | 14.01 | 9.43 | 5.85 | 6.64 |
| Ala | 12.99 | 10.72 | 5.29 | 11.10 |
| Val | 0.00 | 0.00 | 3.63 | 0.42 |
| Ile | 6.59 | 5.90 | 4.46 | 4.07 |
| Leu | 5.33 | 8.96 | 6.84 | 8.32 |
| Tyr | 0.38 | 0.64 | 2.45 | 0.00 |
| Phe | 0.76 | 0.54 | 1.90 | 0.31 |
| His | 2.93 | 1.11 | 3.09 | 1.24 |
| Lys | 4.24 | 8.11 | 6.43 | 8.85 |
| Arg | 3.58 | 2.96 | 6.80 | 1.85 |

The amino terminal sequence of all small and large chain peptides is determined from PVDF blots of the respective electrophoretic peptide bands by automated Edman-degradation in an Applied Biosystems sequencer. The amino-terminal sequences of albumin 1 and 2 are identical. The amino-terminal sequences of albumin 3 are different than those of albumin 1 and 2. However, the amino-terminal sequences of albumin 3 have a high degree of homology to the amino-terminal sequences of albumin 1 and 2 (about 80%). These amino-terminal sequences are most closely related to sequences found in conglutin δ, a sulfur rich 2S protein from *Lupinus angustifolius* L (Gayler, et al.; *Plant Mol. Biol.*; Vol. 15; p. 879; (1990); incorporated herein in its entirety by reference).

To elucidate the differences between the Al peptides, the albumin fractions are further analyzed by isoelectric focusing. The isoelectric point of Al1 is determined at a pH of 6.05, of Al2 at a pH of 5.45 and of Al3 at a pH of 4.95, respectively.

Since the cDNA specific for Al1 and Al3 encode a consensus sequence for asparagine linked N-glycosylation, (see below), concanavalin A binding to albumin-containing fractions is analyzed. None of the Al1 peptides bind concanavalin A, nor are molecular weight size differences apparent in SDS PAGE after N-Glycosidase F treatment. Therefore, N-glycosylation of soybean albumins seems unlikely.

The protein sequencing data, together with the amino acid composition results, indicates the occurrence of the following distinct yet undescribed methionine- and lysine-rich albumin gene products, i.e. Al1 and Al2, and Al3, in soybean seeds. The similarity of the N-terminal Al1 and Al2 amino acid sequences can be explained by the assumption of differential post-translational processing events of the same gene product.

EXAMPLE II.

Isolation of Albumin-specific cDNA Clones from a Soybean Seed cDNA Library RNA isolation, cDNA synthesis and sequence analysis DNA isolation, DNA manipulations, radiolabelling of DNA and hybridizations are done essentially as described by Sambrook, et al.; *Molecular Cloning: A Laboratory Manual*, Cold Spring Harbor (1989); incorporated herein in its entirety by reference.

Soybean plants (*Glycine max* Merr.) are grown in the greenhouse or in the field. Developing, mid-maturation soybean seeds are harvested and stored frozen at −80° C. to be used as a mRNA source for cDNA library construction.

Total RNA is isolated from pooled developing soybean seed (1–15 mm in size). Frozen seeds (1–2 g fresh weight) are ground to a powder in a pestle and mortar, and RNA is isolated according to methods described in Shure, et al.; *Cell*; Vol. 35; p. 225–233; (1983); incorporated herein in its entirety by reference. mRNA is isolated from 1 mg total RNA using an oligo-dT Sepharose spin column according to the manufacture's instructions (Pharmacia, Uppsala, Sweden). Five μg of purified mRNA is used as a template for cDNA synthesis and ligation into Stratagene Lambda Zap II vector arms according to the manufacturer's instructions (Stratagene, La Jolla, Calif.). One hundred ng of size selected cDNA (>500 bp) is ligated to the vector arms and packaged (Stratagene Gigapack Gold) to yield a primary library of $1.2 \times 10^6$ pfu with an average cDNA insert size of 1.2 kb. This library is amplified in *E. coli* Sure cells (Stratagene) to give a titre of $2 \times 10^{10}$ pfu/ml.

Two hundred random plaques are isolated and re-suspended in 500 μl SM. Phagemids (Bluescript S/K) are excised from the Lambda ZAP II vector according to the protocol recommended by Stratagene using helper phage R408 and *E. coli* host strain XL1 Blue. Single colonies are grown overnight in 2 ml of 2×YT medium containing 100 μg/ml ampicillin. The plasmid DNA is isolated by alkaline lysis and ethanol precipitation (Sambrook, et al.; Supra; (1989); incorporated herein in its entirety by reference).

The 5' sequence from 200 individual cDNA clones is obtained using the T3 primer by Taq cycle sequencing on an ABI catalyst 8000 Molecular workstation and ABI 1373A sequenator (Applied Biosystemsy). Sequence data is edited manually to remove vector sequence and a database of the DNA sequence information from the 200 randomly picked cDNA clones using this library is created to facilitate the identification and isolation of cDNA clones encoding abundant expressed polypeptide sequences for which the albumin polypeptides would be an example.

Identification of Albumin Specific cDNA Clones

The cDNA database is searched with back-translated DNA sequences corresponding to the amino terminal sequences of the Al1/2 and Al3 small and large chains using the FASTA® algorithm (Genetics Computer Group, Wisconsin sequence analysis package, Version 8). A section of the deduced amino acid sequence of clone EST 3_38 is found to display an exact match to the amino terminal sequences derived from the small and large chains of Al1. The deduced amino acid sequences of clone EST 2_36, clone EST 3_13, clone EST 3_14 and clone EST 3_62 are found to align exactly with the obtained amino terminal sequences of the Al3 peptides. Furthermore, a computer comparison of the deduced amino acid sequence of clone EST 3_38 and of clone 3_62 with the Genbank sequence data base using the TFASTA® algorithm (Genetics Computer Group) reveal homology to conglutin δ, a sulfur-rich 2S protein from lupin seeds (*Lupinus angustifolius* L.). (Gayler, et al.; Supra; (1990); incorporated herein in its entirety by reference).

An about 600 bp EcoRI fragment from clone EST 3_38 and an about 400 bp EcoRI/SacI fragment from clone EST 3_62 are labeled with [$^{32}$P] dCTP (Amersham) using the Ready Prime kit from Amersham. The labeled fragments are used to screen 15,000 recombinant phages from the cDNA library derived from developing soybean seeds in Lambda ZapII (Stratagene). Approximately 3% of the clones in the library hybridize to both albumin probes.

Forty-five albumin specific phages are randomly selected and the corresponding phagemids are subsequently excised according to the manufacturer's recommendations and sequenced. Among the sequenced clones, 42 are found to be albumin 3 specific (7 encoding the entire coding sequence) and 3 are found to be albumin 1 specific (one encoding the entire coding sequence).

The inserts of the longest identified Al1 and Al3 specific clones, pAl1_42 and pAl3_49, respectively, are sequenced in their entirety (FIGS. 2 and 3) and consequently entered into the Pioneer plasmid collection under the names p9330 and p9331 respectively. Sequence analysis clearly identifies that these clones contain full-length coding sequences, encoding both the N-terminal signal peptides and the stop codon.

Albumin 1 is encoded by 465 base pairs comprised in a 723 base pair cDNA (SEQ ID NO: 1). This cDNA encodes a pre-propeptide having 155 amino acids (SEQ ID NO: 2). The pre-propeptide comprises a 20 amino acid signal peptide, about a 55 amino acid small chain, and about a 80 amino acid large chain. The mature albumin protein comprises two disulfide linked chain, a 4–5 kDa small chain and a 10 kDa large chain. The amino acid composition of the deduced amino acid. Sequence of albumin 1 includes 11.8 mol % methionine and cysteine residues, 9.6 mol % lysine residues and 12.6 mol % asparagine and glutamine residues.

Albumin 3 is encoded by 474 base pairs comprised in a 777 base pair cDNA (SEQ ID NO: 3). This cDNA encodes a pre-propeptide having 158 amino acids (SEQ ID NO: 4). The pre-propeptide comprises a 21 amino acid signal peptide, about a 60 amino acid small chain and a 77 amino acid large chain. The mature albumin 3 contains two disulfide linked chains. The deduced amino acid composition of albumin 3 includes 11.6 mol % methionine and cysteine residues, 10.2 mol % lysine residues, and 13.2 mol % asparagine and glutamine residues.

EXAMPLE III.

To further enhance for the preferred amino acid residues lysine and methionine and to further reduce non-preferred amino acid residues asparagine and glutamine, a cDNA encoding a chimeric albumin, termed albumin 1/3 (Al 1/3) (SEQ ID NO: 6), is prepared based on a GAP alignment (Genetics Computer Group) of the amino-acid sequences of Al1 and Al3 (FIG. 5).

The cDNA clone p9331 (pAl3_49) is modified by oligodexyribonucleotide-directed mutagenesis using the Muta-Gene Phagemid in vitro Mutagenesis kit from BioRad (Hercules, Calif.) based on the Kunkel method (Kunkel, T. A., *Proc. Nat. Acad. Sci. USA*, Vol. 82; p. 488; (1985); incorporated herein in its entirety by reference) according to the manufacturer's recommendations. Mutagenesis is carried out in five consecutive repetitions of in vitro mutagenesis with five oligodeoxyribonucleotide primers. The primers and the changes they confer to the cDNA sequence are summarized in Table 2.

TABLE 2

MUTAGENIC OLIGODEOXYRIBONUCLEOTIDE PRIMERS

| SEQ ID NO: | Oligodeoxyribonucleotide Sequence | Position of Mutagenized Amino Acid Codon in Relation to the Encoded A13 Prepropeptide | Amino acid Codon Changed |
|---|---|---|---|
| 7 | 5'GCTGCCGCAAGCAGCTTAAGGGGGTGAACCTC3' | 36 | Gln to Lys |
| 8 | 5'GGAAGAATCAACTACATACGTAAGAAGGAAGGAAAAGACG3' | 80 | Arg to Lys |
|   |   | 81 | Asn to Lys |
| 9 | 5'GCTGCACAGAAATGAGCGAGCTTAAGAGCCCCAAATGCCAGTGC3' | 105 | Arg to Lys |
| 10 | 5'GGAGGAGAAGGAGAAGAAGAAAATGGAGAAGGAGTTCATGAACTTGGC3' | 129 | Gln to Glu |
|   |   | 138 | Ile to Met |
| 11 | 5'GCAGGTTTGGGCCCATGATCGGGTGCGACTTGTCCTC3' | 151 | Gln to Gly |

Figure 6:
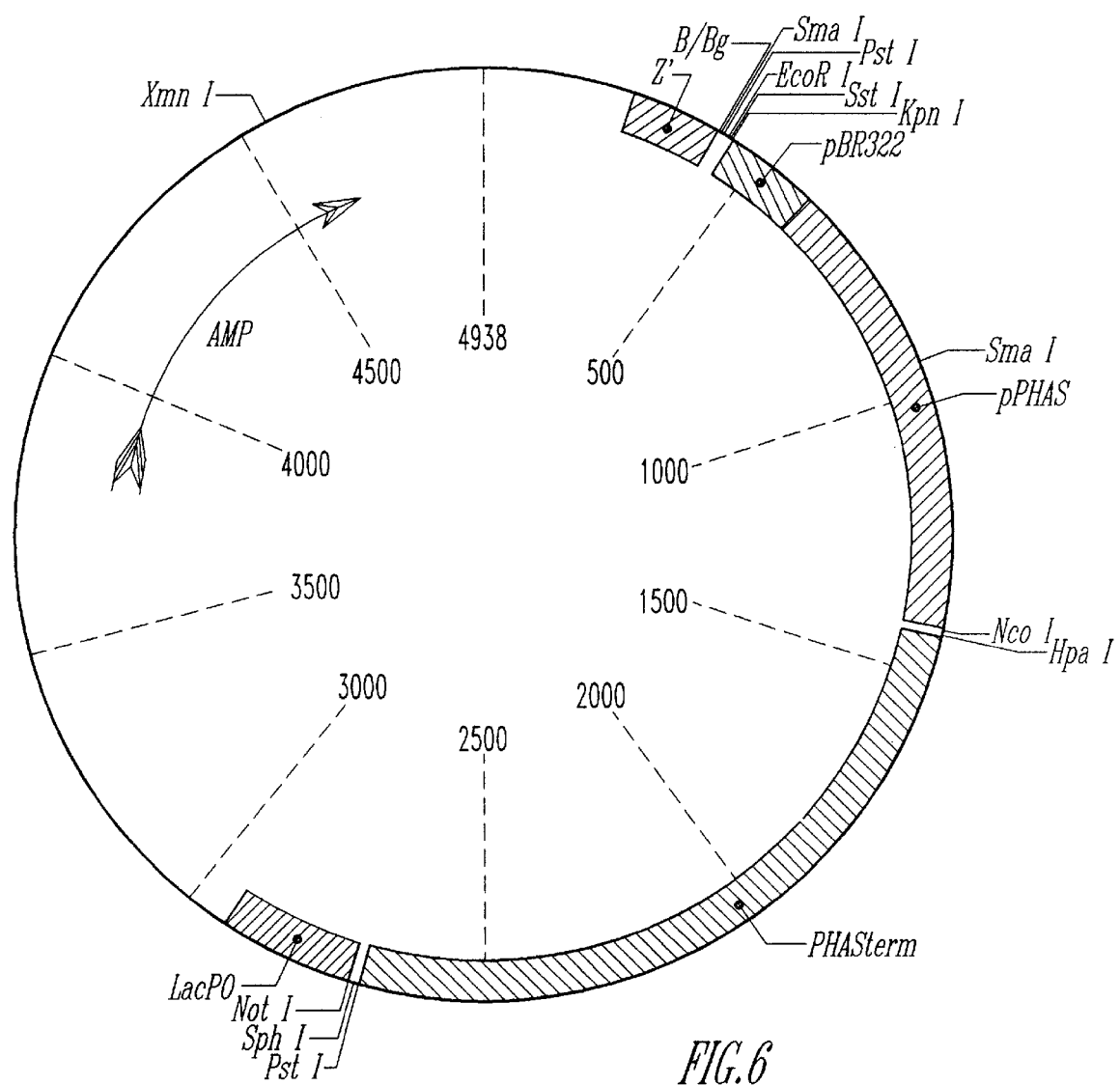
FIG. 6 depicts a plasmid map of p4752.

The amino acid codons at the indicated positions of the cDNA encoding Al3 are essentially only changed into codons which encode preferred amino acids found at the same relative positions (GAP alignement) in the protein sequence of Al1. Thus the resulting amino acid sequence Al 1/3 is termed a chimeric albumin. All changes of amino acid residues are made in sequence regions which are considered important for the protein structure of related 2S albumins from seeds of other plant species and are therefore not obviously amenable for a change. Nevertheless, because the amino acid residues in Al 1/3 are already present in either Al1 or Al3, the structure of the chimeric protein is unlikely to exhibit any deleterious effects when expressed in a seed. Albumin 1/3 has 158 amino acids (FIG. 6). The amino acid composition of albumin 1/3 includes 12.4 mol % methionine and cysteine residues, 13.14 mol % lysine residues, and 10.3 mol % asparagine and glutamine residues.

EXAMPLE IV.

Transformation of *Glycine max* with High Lysine Content and High Sulfur Content Storage Protein Genes Soybean (*Glycine max*) seed, is surface sterilized by exposure to chlorine gas evolved in a glass bell jar. Gas is produced by adding 3.5 ml hydrochloric acid (34–37% w/w) to 100 ml sodium hypochlorite (5.25% w/w). Exposure is for 16–20 hours in a container approximately one cubic foot in volume. Surface sterilized seed is stored in petri dishes at room temperature. Seed is germinated by plating on 1/10 strength agar solidified medium according to Gamborg, et al.; (*Exp. Cell. Res.*; Vol. 50, pp. 151–158; (1968); incorporated herein in its entirety by reference). (B5 basal medium with minimal organics, Sigma Chemical Co., Cat. no. G5893; 0.32 g/L; sucrose, 0.2% w/v and 2-[N-morpholino] ethanesulfonic acid (MES), 3.0 mM) without plant growth regulators and culturing at 28° C. with a 16 hour day length and cool white fluorescent illumination of approximately 20 mEm$^2$S$^1$. After three or four days, seed is prepared for co-cultivation. The seed coat is removed and the elongating radical is removed 3–4 mm below the cotyledons. Ten prepared seeds are held in each of several petri dishes.

Construction of Plant Gene Expression Cassettes

The expression cassette containing one copy of a soybean albumin gene under the control of phaseolin regulatory sequences is the binary plasmid p9127. p9127 is constructed in several steps beginning with oligodeoxynucleotide directed mutagenesis of p9330 (pAl1_42) which contains the full-length cooling sequence of the Al1 protein in the plasmid backbone of Bluescript SK (Stratagene®). Mutagenesis is carried out as described in Example III with oligodeoxyribonucleotide:

1) 5'GCACGAGTCATGACCAAGTCACAATTCTC 3' (SEQ ID NO: 12);

and 2) 5'TCCTCCGATGACTGAGTTAA-CAAAAAAAGTACTAC 3' (SEQ ID NO: 13);

so that an RcaI site is placed and a HindIII site is destroyed at the start of translation and an HpaI site is added just 3' of the stop codon. Upon digestion with the restriction endonucleases RcaI/HpaI, a 472 base-pair DNA sequence corresponding to the full length coding sequence of All is isolated and cloned into p4752 (NcoI/HpaI). p4752 (FIG. 6) contains 883 base pairs of the phaseolin 5' regulatory sequences (i.e. promoter) followed by 84 base pairs of the phaseolin 5' untranslated region. Immediately 3' to these sequences are an NcoI site and HpaI site to facilitate cloning in the 5'→3' direction of an open reading frame resulting in the codon methionine start translation generated by the NcoI site (-CC ATGG) becoming the translational start codon. Downstream of the HpaI site is 1230 base pairs of phaseolin 3' regulatory sequences. p4752 thus contains the phaseolin promoter: phaseolin terminator.

The resulting plasmid, p9069 is then digested with the restriction endonucleases EcoRI/HindIII and the phaseolin promoter: Al1:phaseolin terminator portion is inserted into the EcoRI/HindIII site of plasmid p1830 (=pARC12) (Prosen, et al.; *Biotechnology*; Vol. 5; p. 966; (1987); incorporated herein in its entirety by reference). Plasmid p1830 is a 29.5 kb plasmid which is part of a binary vector system of Agrobacterium and contains the chimeric gene nopaline synthase/neomycine phosphotransferase II as a selectable marker for plant cells.

The plasmid resulting after the insertion of the 2.89 kb fragment of p9069 inserted into p1830 is termed p9127. Plasmid p9127 is about 33 kb in size and confers resistance to tetracycline to the bacterial host.

The plasmid is then transformed to *Agrobacterium tumefaciens* strain LBA 4404 by the freeze/thaw method, known in the art. The presence of the binary plasmid in the resulting bacteria is confirmed by Southern blot analysis.

Preparation of *Agrobacterium tumefaciens* LBA 4404/p9127

Overnight culture of *Agrobacterium tumefaciens* strain LBA 4404 harboring the binary plasmid p9127 grown to log phase in Minimal A medium containing tetracyline, 1.0 mg/ml, is pooled and an optical density measurement at 550 nm is taken. Sufficient volume of the culture is placed in 15 ml conical centrifuge tubes such that upon sedimentation between 1.0 and $2.0 \times 10^{10}$ cells are collected in each tube, where O.D.550 of 1.0=$1.4 \times 10^9$ cells/ml. Sedimentation is by centrifugation at 6000 g for 10 minutes. After centrifugation the supernatant is decanted and the tubes are held at room temperature until inoculum is needed, but not longer than one hour.

Transformation

Inoculations are conducted in batches such that each plate of seed is treated with a newly resuspended pellet of Agrobacterium. One at a time, the pellets are resuspended in 20 ml inoculation medium. Inoculation medium consist of B5 salts (Sigma Chemical Co.), 3.2 g/L; sucrose, 2.0% w/v 6-benzylaminopurine (BAP), 44 mM; indolebutyric acid (IBA), 0.5 mM; acetosyringeone (AS), 100 mM and is buffered to pH 5.5 with MES, 10 mM. Resuspension is by vortexing. The inoculum is then poured into a petri dish containing prepared seed and the cotyledonary nodes are macerated with a surgical blade. This is accomplished by dividing seed in half by longitudinal section through the shoot apex preserving the two whole cotyledons. The two halves of the shoot apex are then broken off their respective cotyledons by prying them away with a surgical blade. The cotyledonary node is then macerated with the surgical blade by repeated scoring along the axis of symmetry. Care is taken not to cut entirely through the explant to the adaxial side. Twenty explants are prepared in roughly 5 minutes and then incubated for 30 minutes at room temperature without agitation. Additional plates are prepared during this time. After 30 minutes the explants are transferred to plates of the same medium solidified with Gelrite (Merck & Co., Inc.), 0.2% w/v. Explants are embedded with the adaxial side up and level with the surface of the medium and cultured at 22° C. for three days under cool white fluorescent light, approximately 20 $mEm^2S^1$.

Culture and Selection

After three days the explants are moved to liquid counterselection medium. Counterselection medium consists of B5 sales, 3.2 g/L; sucrose, 2.0% w/v; BAP, 5.0 mM; IBA 0.5 mM; vancomycin, 200 mg/ml; cefotaxime, 500 mg/ml and is buffered to pH 5.7 with MES, 3 mM. Ten explants are washed in each petri dish with constant, slow gyratory agitation at room temperature for four days. Counterselection medium is replaced four times.

The explants are then picked to agarose solidified selection medium. Selection medium consists of B5 sales, 3.2 g/L; sucrose, 2.0%, w/v; BAP, 5.0 mM; IBA, 0.5 mM; kanamycin sulfate, 50 mg/ml and is buffered to pH 5.7 with MES, 3.0 mM. Selection medium is solidified with SeaKem agarose, 0.3% w/v. The explants are embedded in the medium, adaxial side down and cultured at 28° C. with a 16 hour day length and cool white fluorescent illumination of 60–80 $mEm^2S^1$.

After two weeks explants are again washed with liquid medium on the gyratory shaker. This time the wash is conducted overnight in counterselection medium containing kanamycin sulfate, 50 mg/ml. The following day explants are picked to agarose solidified selection medium. Again they are embedded in the medium, adaxial side down; the culture is as before for another two week period.

Regeneration

After one month on selective media transformed tissue becomes visible as green sectors of regenerating tissue against a background of bleached, less healthy tissue. Explants without green sectors are discarded, explants with green sectors are transferred to elongation medium. Elongation medium consists of B5 salts, 3.2 g/L; sucrose, 2.0% w/v; IBA, 3.3 mM; gibberellic acid, 1.7 mM; vancomycin, 100 mg/ml; cefotaxine, 30 mg/ml; and timentin, 30 mg/ml, buffered to pH 5.7 with MES, 3.0 mM. Elongation medium is solidified with gelrite, 0.2% w/v. They are embedded adaxial side up and cultured as before. Culture is continued on this medium with transfer to fresh plates every two weeks. When shoots become 0.5 cm in length they are excised at the base and placed in rooting medium in 13×100 mm test tubes. Rooting medium consists of B5 salts, 3.2 g/L; sucrose, 15 gm/L; nicotinic acid, 20 mM; pyroglutamic acid (PGA), 900 mg/L and IBA, 10 mM. It is buffered to pH 5.7 with MES, 3.0 mM and solidified with Gelrite, 0.2% w/v. After ten days the shoots are transferred to the same medium without IBA or PGA. Shoots are rooted and held in these tubes under the same environmental conditions as before.

When a root system is well established, the plantlet is transferred to sterile soil mix in plant cons (ICN Biomedicals, Inc., Irvin, Calif., cat no. 26-720 & 1-02). Temperature, photoperiod and light intensity remain the same as before. Under these conditions the regenerates become vigorous, mostly normal (though small) plants. When their root systems again become well established, a corner of the plant cone is cut off and the plants are gradually hardened off in an environmental chamber or greenhouse. Finally they are potted in soil mix and grown to maturity, bearing seed, in a greenhouse.

Growth, Increase, and Harvest of Transgenic Systems

Seed from untransformed and transformed plants of the same variety is planted in the spring and harvested in the fall. Each individual line is kept separate while grown in one or more 10.5 foot rows for maximum increase.

The determination of the levels of a particular protein can be determined by methods well known in the art including, but not limited to enzyme linked immunoassays, immunofluorescent assays, Western blot analysis and immunoprecipitation analyses.

The amino acid content of seeds from transformed and untransformed plants is analyzed by methods described in the *Office Methods of Analysis of the AOAC*, Hilrich (ed.), AOAc International; Vol. 2; p. 1096; (1990); incorporated in its entirety by reference.

EXAMPLE IV

Preparation of Albumin-specific Antibodies

Antibodies specific for albumin polypeptides are produced by injecting female New Zealand white rabbits (Bethyl Laboratory, Montgomery, Tex.) six times with homogenized polyacrylamide gel slices containing 100 μg of PAGE purified albumin. Animals are then bled at two week intervals. The antibodies are further purified by affinity-chromatography with Affigel 15(BioRad)-immobilized antigen as described by Harlow, et al.; *Antibodies: A Laboratory Manual*, Cold Spring Harbor, N.Y.; (1988); incorporated herein in its entirety by reference. The affinity column is prepared with purified albumin 3 essentially is recommended by BioRad®. Immune detection of antigens on PVDF blots is carried out following the protocol of Meyer, et al.; *J. Cell. Biol.*; Vol. 107; p. 163; (1988); incorporated herein in its entirety by reference, using the ECL kit from Amersham (Arlington Heights, Ill.).

All publications and patents are incorporated by reference herein, as though individually incorporated by reference. The invention is not limited to the exact details shown and described, for it should be understood that many variations and modifications may be made while remaining within the spirit and scope of the invention defined by the claims.

What is claimed is:

1. An isolated DNA molecule comprising a preselected DNA segment which encodes a protein having SEQ ID NOS: 2, 4 or 6.

2. An expression cassette comprising the DNA molecule of claim 1 operably linked to a promoter functional in a host plant cell.

3. The expression cassette of claim 2 wherein the promoter is a seed-specific promoter.

4. A fertile transformed plant containing the isolated preselected DNA segment of claim 2.

5. The plant of claim 4 which is a soybean plant.

6. A method of increasing the nutritional value of a seed comprising:

a) introducing into the cells of a plant the expression cassette of claim 3 to produce transformed plant cells;

b) regenerating a transformed plant from the transformed cells; and c) isolating seeds from the regenerated transformed plant.

7. The method of claim 6 wherein the plant is a soybean plant.

8. The method of claim 6 wherein lysine, methionine, cysteine or combinations thereof are present in the seed in an amount greater than the amount in a seed of a corresponding untransformed plant.

9. The method of claim 8 wherein lysine is present in the seed in an amount at least about 5% greater than the amount in a seed of a corresponding untransformed plant.

10. The method of claim 8 wherein methionine and cysteine are present in the seed in an amount at least about 15% greater than the amount in a seed of a corresponding untransformed plant.

11. A seed produced by the method of claim 6.

12. A plant produced from the seed of claim 11.

13. An isolated DNA molecule comprising a preselected DNA segment comprising the sequence of SEQ ID NOS: 1, 3 or 5.

14. A DNA molecule wherein SEQ ID NOS: 1 or 3 are modified by site-directed mutagenesis to encode for a protein with increased levels of lysine, methionine, cysteine or combinations thereof.

15. A DNA molecule wherein SEQ ID NOS: 1 or 3 are modified by site-directed mutagenesis to encode for a protein with decreased levels of asparagine and/or glutamine.

16. An expression cassette comprising the DNA molecule of claim 13 operably linked to a promoter functional in a host plant cell.

17. The expression cassette of claim 16 wherein the promoter is a seed-specific promoter.

18. A fertile transformed plant containing the preselected DNA segment of claim 13.

19. The plant of claim 18 wherein the preselected DNA segment encodes an endogenous polypeptide sequence.

20. The plant of claim 18 which is a soybean plant.

21. The plant of claim 20 wherein the preselected DNA segment encodes a soybean albumin.

22. A method of increasing the nutritional value of a seed comprising:

a) introducing into the cells of a plant the expression cassette of claim 16 to produce transformed plant cells;

b) regenerating a transformed plant from the transformed cells; and c) isolating seeds from the regenerated transformed plant.

23. The method of claim 22 wherein the plant is a soybean plant.

24. The method of claim 23 wherein lysine, methionine, cysteine or combinations thereof are present in the seed in an amount greater than the amount in a seed of a corresponding untransformed plant.

25. The method of claim 24 wherein lysine is present in the seed in an amount at least about 5% greater than the amount in the seed of a corresponding untransformed plant.

26. The method of claim 24 wherein methionine and cysteine are present in the seed in an amount at least about 15% greater than the amount in the seed of a corresponding untransformed plant.

27. A seed produced by the method of claim 22.

28. A plant produced from the seed of claim 27.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 723 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 10..474

( x i ) SEQUENCE DESCRIPTION: SEQ ID NO:1:

```
GCACGAGAA ATG ACC AAG CTT ACA ATT CTC CTC ATC GCT CTT CTC TTC              48
          Met Thr Lys Leu Thr Ile Leu Leu Ile Ala Leu Leu Phe
           1           5                      10

ATC GCC CAC ACC TGC TGC GCC TCC AAA TGG CAA CAG CAC CAG CAA GAG            96
Ile Ala His Thr Cys Cys Ala Ser Lys Trp Gln Gln His Gln Gln Glu
     15                  20                  25

AGC TGC CGC GAG CAG CTC AAG GGG ATC AAC CTC AAC CCC TGT GAG CAC           144
Ser Cys Arg Glu Gln Leu Lys Gly Ile Asn Leu Asn Pro Cys Glu His
 30                  35                  40                  45

ATC ATG GAG AAG ATC CAA GCT GGC CGC CGC GGC GAG GAC GGC AGC GAC           192
Ile Met Glu Lys Ile Gln Ala Gly Arg Arg Gly Glu Asp Gly Ser Asp
                 50                  55                  60

GAA GAT CAC ATT CTC ATC AGG ACC ATG CCG GGA AGA ATC AAC TAC ATC           240
Glu Asp His Ile Leu Ile Arg Thr Met Pro Gly Arg Ile Asn Tyr Ile
                 65                  70                  75

AGG AAG AAG GAA GGA AAA GAA GAA GAA GAA GAA GGA CAC ATG CAG AAG           288
Arg Lys Lys Glu Gly Lys Glu Glu Glu Glu Glu Gly His Met Gln Lys
             80                  85                  90

TGC TGC AGC GAA ATG AGC GAG CTG AAA AGC CCC ATA TGC CAG TGC AAA           336
Cys Cys Ser Glu Met Ser Glu Leu Lys Ser Pro Ile Cys Gln Cys Lys
         95                  100                 105

GCG CTA CAG AAG ATA ATG GAT AAC CAG AGC GAG CAA CTG GAG GGG AAG           384
Ala Leu Gln Lys Ile Met Asp Asn Gln Ser Glu Gln Leu Glu Gly Lys
110                 115                 120                 125

GAG AAG AAG CAG ATG GAG AGA GAG CTC ATG AAC TTG GCT ATT AGG TGC           432
Glu Lys Lys Gln Met Glu Arg Glu Leu Met Asn Leu Ala Ile Arg Cys
                 130                 135                 140

AGG TTG GGA CCC ATG ATA GGG TGC GAC TTG TCC TCC GAT GAC                   474
Arg Leu Gly Pro Met Ile Gly Cys Asp Leu Ser Ser Asp Asp
                 145                 150                 155

TGAAAAAAAA GTACTACTAA CACATATATG TGTTAGTTTA TGCTAGCTAG AAGAACGTAT         534

AAGCTATCTC CGTATGTTGT ATATTAATAA AAAGATCATC ACTGGTGAAT GGTGATCGTG         594

TATGTAACGT AGTGGGCAAT GGAAGCACTT AGAGTGTGCT TTGTGGCCTT GCCCTCTGTT         654

TTGATAACTG AGACTTTTGC GAATACCGTT CGTTTTCCC TTCAAAAAAA AAAAAAAAA           714

AAAAAAAA                                                                  723
```

( 2 ) INFORMATION FOR SEQ ID NO:2:

( i ) SEQUENCE CHARACTERISTICS:
        ( A ) LENGTH: 155 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Lys  Leu  Thr  Ile  Leu  Leu  Ile  Ala  Leu  Leu  Phe  Ile  Ala  His
 1              5                        10                       15

Thr  Cys  Cys  Ala  Ser  Lys  Trp  Gln  Gln  His  Gln  Gln  Glu  Ser  Cys  Arg
              20                       25                       30

Glu  Gln  Leu  Lys  Gly  Ile  Asn  Leu  Asn  Pro  Cys  Glu  His  Ile  Met  Glu
         35                       40                       45

Lys  Ile  Gln  Ala  Gly  Arg  Arg  Gly  Glu  Asp  Gly  Ser  Asp  Glu  Asp  His
     50                       55                       60

Ile  Leu  Ile  Arg  Thr  Met  Pro  Gly  Arg  Ile  Asn  Tyr  Ile  Arg  Lys  Lys
65                       70                       75                       80

Glu  Gly  Lys  Glu  Glu  Glu  Glu  Glu  Gly  His  Met  Gln  Lys  Cys  Cys  Ser
              85                       90                       95

Glu  Met  Ser  Glu  Leu  Lys  Ser  Pro  Ile  Cys  Gln  Cys  Lys  Ala  Leu  Gln
             100                      105                      110

Lys  Ile  Met  Asp  Asn  Gln  Ser  Glu  Gln  Leu  Glu  Gly  Lys  Glu  Lys  Lys
         115                      120                      125

Gln  Met  Glu  Arg  Glu  Leu  Met  Asn  Leu  Ala  Ile  Arg  Cys  Arg  Leu  Gly
         130                      135                      140

Pro  Met  Ile  Gly  Cys  Asp  Leu  Ser  Ser  Asp  Asp
145                      150                      155
```

( 2 ) INFORMATION FOR SEQ ID NO:3:

( i ) SEQUENCE CHARACTERISTICS:
        ( A ) LENGTH: 777 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 28..501

( x i ) SEQUENCE DESCRIPTION: SEQ ID NO:3:

```
GAGCTCGTGC  CGAATCGGCA  CGAGAAA  ATG  ACC  AAG  TTC  ACA  ATC  CTC  CTC         51
                                Met  Thr  Lys  Phe  Thr  Ile  Leu  Leu
                                                          160

ATC  TCT  CTT  CTC  TTC  TGC  ATC  GCC  CAC  ACT  TGC  AGC  GCC  TCC  AAA  TGG  99
Ile  Ser  Leu  Leu  Phe  Cys  Ile  Ala  His  Thr  Cys  Ser  Ala  Ser  Lys  Trp
     165                      170                      175

CAG  CAC  CAG  CAA  GAT  AGC  TGC  CGC  AAG  CAG  CTC  CAG  GGG  GTG  AAC  CTC 147
Gln  His  Gln  Gln  Asp  Ser  Cys  Arg  Lys  Gln  Leu  Gln  Gly  Val  Asn  Leu
180                      185                      190                      195

ACG  CCC  TGC  GAG  AAG  CAC  ATC  ATG  GAG  AAG  ATC  CAA  GGC  CGC  GGC  GAT 195
Thr  Pro  Cys  Glu  Lys  His  Ile  Met  Glu  Lys  Ile  Gln  Gly  Arg  Gly  Asp
         200                      205                      210

GAC  GAT  GAT  GAT  GAT  GAC  GAC  GAC  AAT  CAC  ATT  CTC  AGG  ACC  ATG  CGG 243
Asp  Asp  Asp  Asp  Asp  Asp  Asp  Asp  Asn  His  Ile  Leu  Arg  Thr  Met  Arg
              215                      220                      225

GGA  AGA  ATC  AAC  TAC  ATA  AGG  AGG  AAC  GAA  GGA  AAA  GAC  GAA  GAC  GAA 291
Gly  Arg  Ile  Asn  Tyr  Ile  Arg  Arg  Asn  Glu  Gly  Lys  Asp  Glu  Asp  Glu
```

-continued

```
                230                         235                         240
GAA   GAA   GAA   GGA   CAC   ATG   CAG   AAG   TGC   TGC   ACA   GAA   ATG   AGC   GAG   CTG        339
Glu   Glu   Glu   Gly   His   Met   Gln   Lys   Cys   Cys   Thr   Glu   Met   Ser   Glu   Leu
            245                           250                           255

AGA   AGC   CCC   AAA   TGC   CAG   TGC   AAA   GCG   CTG   CAG   AAG   ATA   ATG   GAG   AAC        387
Arg   Ser   Pro   Lys   Cys   Gln   Cys   Lys   Ala   Leu   Gln   Lys   Ile   Met   Glu   Asn
260                           265                           270                           275

CAG   AGC   GAG   GAA   CTG   GAG   GAG   AAG   CAG   AAG   AAA   ATG   GAG   AAG   GAG              435
Gln   Ser   Glu   Glu   Leu   Glu   Glu   Lys   Gln   Lys   Lys   Met   Glu   Lys   Glu
                        280                           285                           290

CTC   ATT   AAC   TTG   GCT   ACT   ATG   TGC   AGG   TTT   GGA   CCC   ATG   ATC   CAG   TGC        483
Leu   Ile   Asn   Leu   Ala   Thr   Met   Cys   Arg   Phe   Gly   Pro   Met   Ile   Gln   Cys
            295                           300                           305

GAC   TTG   TCC   TCC   GAT   GAC   TAAGAAGTTA  AAAGCAATGT  TGTCACTTGT                               531
Asp   Leu   Ser   Ser   Asp   Asp
                        310

ACGTACTAAC  ACATGATGTG  ATAGTTTATG  CTAGCTAGCT  ATAACATAAG  CTGTCTGTGA                               591

GTGTGTTGTA  TATTAATAAA  GATCATCACT  GGTGAATGGT  GATCGTGTAC  GTACCCTACT                               651

TAGTAGGCAA  TGGAAGCACT  TAGAGTGTGC  TTTGTGCATG  GCCTTGCCTC  TGTTTTGAGA                               711

CTTTTGTAAT  GTTTTCGAGT  TTAAATCTTT  GCCTTTGCGG  AAAAAAAAAA  AAAAAAAAA                                771

AAAAAA                                                                                              777
```

( 2 ) INFORMATION FOR SEQ ID NO:4:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met   Thr   Lys   Phe   Thr   Ile   Leu   Leu   Ile   Ser   Leu   Leu   Phe   Cys   Ile   Ala
1                       5                           10                          15

His   Thr   Cys   Ser   Ala   Ser   Lys   Trp   Gln   His   Gln   Gln   Asp   Ser   Cys   Arg
                  20                          25                          30

Lys   Gln   Leu   Gln   Gly   Val   Asn   Leu   Thr   Pro   Cys   Glu   Lys   His   Ile   Met
            35                          40                          45

Glu   Lys   Ile   Gln   Gly   Arg   Gly   Asp   Asp   Asp   Asp   Asp   Asp   Asp   Asp   Asp
      50                          55                          60

Asn   His   Ile   Leu   Arg   Thr   Met   Arg   Gly   Arg   Ile   Asn   Tyr   Ile   Arg   Arg
65                          70                          75                          80

Asn   Glu   Gly   Lys   Asp   Glu   Asp   Glu   Glu   Glu   Gly   His   Met   Gln   Lys
                        85                          90                          95

Cys   Cys   Thr   Glu   Met   Ser   Glu   Leu   Arg   Ser   Pro   Lys   Cys   Gln   Cys   Lys
                  100                         105                         110

Ala   Leu   Gln   Lys   Ile   Met   Glu   Asn   Gln   Ser   Glu   Glu   Leu   Glu   Glu   Lys
            115                         120                         125

Gln   Lys   Lys   Lys   Met   Glu   Lys   Glu   Leu   Ile   Asn   Leu   Ala   Thr   Met   Cys
      130                         135                         140

Arg   Phe   Gly   Pro   Met   Ile   Gln   Cys   Asp   Leu   Ser   Ser   Asp   Asp
145                         150                         155
```

( 2 ) INFORMATION FOR SEQ ID NO:5:

( i ) SEQUENCE CHARACTERISTICS:
        ( A ) LENGTH: 777 base pairs
        ( B ) TYPE: nucleic acid ( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 28..501

( x i ) SEQUENCE DESCRIPTION: SEQ ID NO:5:

```
GAGCTCGTGC CGAATCGGCA CGAGAAA ATG ACC AAG TTC ACA ATC CTC CTC           51
                                 Met Thr Lys Phe Thr Ile Leu Leu
                                 160                         165

ATC TCT CTT CTC TTC TGC ATC GCC CAC ACT TGC AGC GCC TCC AAA TGG         99
Ile Ser Leu Leu Phe Cys Ile Ala His Thr Cys Ser Ala Ser Lys Trp
            170                 175                 180

CAG CAC CAG CAA GAT AGC TGC CGC AAG CAG CTT AAG GGG GTG AAC CTC        147
Gln His Gln Gln Asp Ser Cys Arg Lys Gln Leu Lys Gly Val Asn Leu
            185                 190                 195

ACG CCC TGC GAG AAG CAC ATC ATG GAG AAG ATC CAA GGC CGC GGC GAT        195
Thr Pro Cys Glu Lys His Ile Met Glu Lys Ile Gln Gly Arg Gly Asp
    200                 205                 210

GAC GAT GAT GAT GAT GAC GAC GAC AAT CAC ATT CTC AGG ACC ATG CGG        243
Asp Asp Asp Asp Asp Asp Asp Asp Asn His Ile Leu Arg Thr Met Arg
215                 220                 225                 230

GGA AGA ATC AAC TAC ATA CGT AAG AAG GAA GGA AAA GAC GAA GAC GAA        291
Gly Arg Ile Asn Tyr Ile Arg Lys Lys Glu Gly Lys Asp Glu Asp Glu
                235                 240                 245

GAA GAA GAA GGA CAG ATG CAG AAG TGC TGC ACA GAA ATG AGC GAG CTT        339
Glu Glu Glu Gly Gln Met Gln Lys Cys Cys Thr Glu Met Ser Glu Leu
            250                 255                 260

AAG AGC CCC AAA TGC CAG TGC AAA GCG CTG CAG AAG ATA ATG GAG AAC        387
Lys Ser Pro Lys Cys Gln Cys Lys Ala Leu Gln Lys Ile Met Glu Asn
        265                 270                 275

CAG AGC GAG GAA CTG GAG GAG AAG GAG AAC AAG AAA ATG GAG AAG GAG        435
Gln Ser Glu Glu Leu Glu Glu Lys Glu Asn Lys Lys Met Glu Lys Glu
    280                 285                 290

CTT ATG AAC TTG GCT ACT ATG TGC AGG TTT GGG CCC ATG ATC GGA TGC        483
Leu Met Asn Leu Ala Thr Met Cys Arg Phe Gly Pro Met Ile Gly Cys
295                 300                 305                 310

GAC TTG TCC TCC GAT GAC TAAGAAGTTA AAAGCAATGT TGTCACTTGT               531
Asp Leu Ser Ser Asp Asp
                315

ACGTACTAAC ACATGATGTG ATAGTTTATG CTAGCTAGCT ATAACATAAG CTGTCTCTGA      591

GTGTGTTGTA TATTAATAAA GATCATCACT GGTGAATGGT GATCGTGTAC GTACCCTACT      651

TAGTAGGCAA TGGAAGCACT TAGAGTGTGC TTTGTGCATG GCCTTGCCTC TGTTTTGAGA      711

CTTTTGTAAT GTTTTCGAGT TAAATCTTT GCCTTTGCGG AAAAAAAAAA AAAAAAAAA        771

AAAAAA                                                                 777
```

( 2 ) INFORMATION FOR SEQ ID NO:6:

( i ) SEQUENCE CHARACTERISTICS:
( A ) LENGTH: 158 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Thr Lys Phe Thr Ile Leu Leu Ile Ser Leu Leu Phe Cys Ile Ala
1               5                   10                  15
```

| | | | | | | | | | | | | | | |
|---|---|---|---|---|---|---|---|---|---|---|---|---|---|---|
|His|Thr|Cys|Ser|Ala|Ser|Lys|Trp|Gln|His|Gln|Gln|Asp|Ser|Cys|Arg
| | | |20| | | |25| | | | |30| | |

Lys Gln Leu Lys Gly Val Asn Leu Thr Pro Cys Glu Lys His Ile Met
           35              40              45

Glu Lys Ile Gln Gly Arg Gly Asp Asp Asp Asp Asp Asp Asp
     50              55              60

Asn His Ile Leu Arg Thr Met Arg Gly Arg Ile Asn Tyr Ile Arg Lys
65              70              75              80

Lys Glu Gly Lys Asp Glu Asp Glu Glu Glu Glu Gly Gln Met Gln Lys
            85              90              95

Cys Cys Thr Glu Met Ser Glu Leu Lys Ser Pro Lys Cys Gln Cys Lys
            100             105             110

Ala Leu Gln Lys Ile Met Glu Asn Gln Ser Glu Glu Leu Glu Glu Lys
         115             120             125

Glu Asn Lys Lys Met Glu Lys Glu Leu Met Asn Leu Ala Thr Met Cys
    130             135             140

Arg Phe Gly Pro Met Ile Gly Cys Asp Leu Ser Ser Asp Asp
145             150             155

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:7:

GCTGCCGCAA GCAGCTTAAG GGGGTGAACC TC                             32

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:8:

GGAAGAATCA ACTACATACG TAAGAAGGAA GGAAAAGACG                  40

( 2 ) INFORMATION FOR SEQ ID NO:9:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:9:

GCTGCACAGA AATGAGCGAG CTTAAGAGCC CCAAATGCCA GTGC            44

( 2 ) INFORMATION FOR SEQ ID NO:10:

( i ) SEQUENCE CHARACTERISTICS:
        ( A ) LENGTH: 48 base pairs

-continued ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "Primer"

( x i ) SEQUENCE DESCRIPTION: SEQ ID NO:10:

GGAGGAGAAG GAGAAGAAGA AAATGGAGAA GGAGTTCATG AACTTGGC    48

( 2 ) INFORMATION FOR SEQ ID NO:11:

( i ) SEQUENCE CHARACTERISTICS:
       ( A ) LENGTH: 37 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "Primer"

( x i ) SEQUENCE DESCRIPTION: SEQ ID NO:11:

GCAGGTTTGG GCCCATGATC GGGTGCGACT TGTCCTC    37

( 2 ) INFORMATION FOR SEQ ID NO:12:

( i ) SEQUENCE CHARACTERISTICS:
       ( A ) LENGTH: 29 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "Primer"

( x i ) SEQUENCE DESCRIPTION: SEQ ID NO:12:

GCACGAGTCA TGACCAAGTC ACAATTCTC    29

( 2 ) INFORMATION FOR SEQ ID NO:13:

( i ) SEQUENCE CHARACTERISTICS:
       ( A ) LENGTH: 35 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "Primer"

( x i ) SEQUENCE DESCRIPTION: SEQ ID NO:13:

TCCTCCGATG ACTGAGTTAA CAAAAAAAGT ACTAC    35